(12) United States Patent
Uemura et al.

(10) Patent No.: US 7,211,425 B2
(45) Date of Patent: May 1, 2007

(54) SERINE PROTEASE BSSP4

(75) Inventors: Hidetoshi Uemura, Hyogo (JP); Akira Okui, Nara (JP); Katsuya Kominami, Osaka (JP); Nozomi Yamaguchi, Kyoto (JP); Shinichi Mitsui, Kyoto (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 11/476,636

(22) Filed: Jun. 29, 2006

(65) Prior Publication Data

US 2006/0239994 A1    Oct. 26, 2006

Related U.S. Application Data

(62) Division of application No. 10/884,163, filed on Jul. 6, 2004, which is a division of application No. 09/856,298, filed as application No. PCT/JP99/06472 on Nov. 19, 1999, now abandoned.

(30) Foreign Application Priority Data

Nov. 20, 1998  (JP)  ................................. 10/347813

(51) Int. Cl.
*C12N 9/64* (2006.01)
*C12N 15/57* (2006.01)
*C12N 15/70* (2006.01)
*C12N 15/89* (2006.01)

(52) U.S. Cl. ..................................... 435/226
(58) Field of Classification Search ...................... None
See application file for complete search history.

(56) References Cited

U.S. PATENT DOCUMENTS

| | | | |
|---|---|---|---|
| 5,834,290 A | 11/1998 | Engelrud et al. | |
| 6,426,199 B1 | 7/2002 | Darrow et al. | |
| 6,479,274 B1 * | 11/2002 | Antalis et al. | 435/252.3 |
| 6,635,468 B2 * | 10/2003 | Ashkenazi et al. | 435/252.3 |
| 6,664,376 B2 * | 12/2003 | Ashkenazi et al. | 530/350 |
| 6,686,451 B1 * | 2/2004 | Desnoyers et al. | 530/387.1 |
| 6,723,535 B2 * | 4/2004 | Ashkenazi et al. | 435/69.1 |
| 6,767,995 B2 * | 7/2004 | Desnoyers et al. | 530/387.1 |
| 6,806,352 B2 * | 10/2004 | Desnoyers et al. | 530/350 |
| 6,818,449 B2 * | 11/2004 | Fong et al. | 435/325 |
| 6,818,746 B2 * | 11/2004 | Goddard et al. | 530/350 |
| 6,828,146 B2 * | 12/2004 | Desnoyers et al. | 435/325 |
| 6,908,756 B1 * | 6/2005 | Uemura et al. | 435/212 |
| 6,921,658 B1 * | 7/2005 | Uemura et al. | 435/226 |
| 6,998,245 B1 * | 2/2006 | Uemura et al. | 435/7.4 |
| 2002/0132240 A1 | 9/2002 | Ashkenazi et al. | |
| 2002/0146709 A1 | 10/2002 | Ashkenazi et al. | |
| 2002/0160374 A1 | 10/2002 | Ashkenazi et al. | |
| 2002/0192659 A1 | 12/2002 | Ashkenzai et al. | |
| 2002/0197671 A1 | 12/2002 | Ashkenazi et al. | |
| 2002/0198366 A1 | 12/2002 | Ashkenazi et al. | |

FOREIGN PATENT DOCUMENTS

| | | |
|---|---|---|
| EP | 0 828 003 A2 | 3/1998 |
| JP | 10-117789 | 5/1998 |
| JP | 10-146188 | 6/1998 |
| WO | WO 98/36054 | 8/1998 |
| WO | WO 99/14328 | 3/1999 |
| WO | WO 99/35170 | 7/1999 |

OTHER PUBLICATIONS

Davies et al., "Serine Proteases in Rodent Hippocampus", *The Journal of Biological Chemistry*, vol. 273, No. 36, pp. 23004-23011 (Sep. 4, 1998).
Yamashiro et al., "Molecular Cloning of a Novel Trypsin-Like Serine Protease (Neurosin) Preferentially Expressed in Brain", *Biochimica et Biophysica Acta*, vol. 1350, pp. 11-14 (1997).
Abstract: DATABASE EMBL [Online], Nov. 9, 1998, Strausberg, R., "qx53f04.x1 NCI_CGAP_Pan1 *Homo sapiens* cDNA clone", Database accession No. A1249364, XP002234200.
Abstract: DATABASE EMBL [Online], Mar. 30, 1998, Strausberg, R., "am27d01.s1 Soares_NFL_t_GBC_S1 *Homo sapiens* cDNA clone", Database accession No. AA884001, XP002234201.
Abstract: DATABASE EMBL [Online], Jan. 7, 1998, Ricke et al., "*Homo sapiens* chromosome 16", Database accession No. AC003965, XP002234202.

* cited by examiner

*Primary Examiner*—Nashaat T. Nashed
*Assistant Examiner*—William W. Moore
(74) *Attorney, Agent, or Firm*—Browdy & Neimark, PLLC

(57) ABSTRACT

There are provided proteins having the amino acid sequences represented by SEQ ID NOS: 2, 4, 6, 8, 10, 12, 14, 16, 18 and 20; proteins having amino acid sequences derived from these amino acid sequences by deletion, substitution or addition of one to several amino acids; and nucleotide sequences encoding the same; transgenic non-human animals with altered expression level of a serine protease BSSP4; an antibody against BSSP4; and a method for detecting BSSP4 in a specimen by using the antibody.

2 Claims, 7 Drawing Sheets

SERINE PROTEASE BSSP4

CROSS-REFERENCE TO RELATED APPLICATIONS

This is a divisional of application Ser. No. 10/884,163, filed Jul. 6, 2004, which is a divisional of application Ser. No. 09/856,298, filed May 21, 2001, now abandoned, which is a 371 national stage application of PCT/JP99/06472, filed Nov. 19, 1999, the entire contents of these applications are incorporated herein by reference.

FIELD OF THE INVENTION

The present invention relates to isolated polynucleotides of human and mouse serine proteases (hereinafter referred to as "hBSSP4" and "mBSSP4", respectively, and, in case no differentiation thereof from each other is needed, simply referred to as "BSSP4"), and their homologous forms, mature forms, precursors and polymorphic variants as well as a method for detecting thereof. Further, it relates to hBSSP4 and mBSSP4 proteins, compositions containing hBSSP4 and mBSSP4 polynucleotides and proteins, as well as their production and use.

BACKGROUND OF THE INVENTION

In general, proteases are biosynthesized as inactive precursors. They undergo limited hydrolysis in molecules to convert into activated type proteases. In so far as enzymes are proteases, they have an activity for hydrolyzing a peptide bond, while their action modes are varied according to kinds of proteases. According to a particular kind of catalytic site, proteases are divided into serine proteases, cysteine proteases, aspartate proteases, metal proteases and the like. Proteases of each kind have a variety of properties, ranging from a protease having general digestive properties to a protease having various regulatory domains and strict substrate specificity, thereby specifically hydrolyzing only characteristic proteins.

Further, proteins undergo various processing even after translation to produce active proteins. In many secretory proteins, a protein are first synthesized on the ribosome in cytoplasm as an inactive precursor (pro-form) which comprises an active protein bearing at the N-terminus thereof a peptide of about 15 to 60 amino acids responsible for secretion (secretory signal). This peptide region is concerned with the mechanism for passing through the cell membrane and is removed upon cleavage by a specific protease during the passage through the membrane, in almost all the cases, to produce a mature protein. A secretory signal has a broad hydrophobic region comprising hydrophobic amino acids in the middle of the sequence, and basic amino acid residues at a site close to the N-terminus. A secretory signal is a synonym of a signal peptide. In addition, in some proteins, a peptide moiety which functions as a secretory signal is further attached to the N-terminus of the inactive precursor (pro-form). Such a protein is called a prepro-protein (prepro-form).

For example, trypsin is present as a prepro-form immediately after translation into amino acids. After being secreted from cells, it is present as a pro-form and is converted into active trypsin in duodenum upon limited hydrolysis by enteropeptidase or by trypsin itself.

The optimal pH range of serine proteases is neutral to weak alkaline and, in general, many of them have a molecular weight of about 30,000 or lower. All proteases of blood coagulation, fibrinolysis and complement systems having a large molecular weight belong to trypsin-like serine proteases. They have many regulator domains and form a protease cascade which is of very importance to reactions in a living body.

Recently, cDNAs and amino acid sequences of many novel proteases have been determined by PCR for consensus sequences of serine proteases using oligonucleotide primers. According to this method, novel proteases have been found by various researchers such as Yamamura et al. (Yamanura, Y et al., Biochem. Biophys. Res. Commun., 239, 386, 1997), Gschwend, et al. (Gschwend, T. P. et al., Mol. Cell. Neurosci., 9. 207, 1997), Chen et al. (Chen, Z-L, et al., J. Neurosci., 15, 5088, 1995) and others.

SEQ ID NO: 3 of JP 9-149790 A discloses neurosin as a novel serine protease. Neurosin has also been reported in Biochimica et Byophysica Acta, 1350, 11–14, 1997. By this, there is provided a method for mass production of neurosin using the serine protease gene and a method for screening specific inhibitors using the enzyme. In addition, the screening method has been shown to be useful for screening medicines for treating various diseases.

Serine proteases expressed in a brain-nerve system such as neurosin are considered to play various roles in the brain-nerve system. Therefore, there is a possibility that isolation of a gene encoding a novel protease expressed in a brain-nerve system and production of a protein using the gene would be useful for diagnosis or treatment of various diseases related to the brain-nerve system.

Nowadays, in general, clinical diagnosis of Alzheimer's disease is conducted based on the diagnosis standard of DSM-IIIR and NINCDS-ADRDA (Mckhann, G. et al., Neurology, 34. 939, 1994) or the diagnosis standard of DSM-IV (American Psychiatric Association; Diagnostic and statistical manuals of mental disorders, 4th ed., Washington D.C., American Psychiatric Association, 1994). However, these standards are conditioned by decline of recognition functions which causes a severe disability in a daily life or a social life. Then, it is pointed out that the diagnosis is less scientific objectivity because the diagnosis may be influenced by the level of an individual's social life and further the specialty and experience of a physician who diagnoses particular conditions. In addition, definite diagnosis of Alzheimer's disease is conducted by pathohistological analyses and, in this respect, substantial inconsistency between clinical diagnosis and autopsy diagnosis is pointed out.

At present, image diagnosis is employed as a supplemental means in clinical diagnosis of Alzheimer's diagnosis and it is possible to analyze brain functions, for example, decline of metabolism and atrophy in specific sites such as hippocampus, parietal lobe of cerebral cortex and the like which are specific for Alzheimer's disease by PET and SPECT. However, to define Alzheimer's disease based on lowering of a blood flow from parietal lobe to temporal lobe is very dangerous. In addition, there is few report showing that MRS testicle useful for patients with dementia including those of Alzheimer's disease. Further, although CT-MRI image diagnosis is used, a lesion of white matter such as atrophy of brain, PVL or the like is not specific for Alzheimer type dementia. Since it has been reported that atrophy of brain proceeds as getting older, the above observation is not necessarily found in Alzheimer type dementia. Furthermore, since an image obtained by MRI varies according to strength of a magnetic field, performance of an apparatus and imaging conditions, numerical data obtain in different facilities cannot be compared with each other except atrophic change. In addition, there is a limit to image measurement. Further, enlargement of ventricle can be recognized in vascular dementia cases and there are cases wherein atrophy of hippocampus is observed after ischemia of basilar artery.

Under these circumstances, many researchers have requested to develop biological diagnosis markers as a means for providing better precision and objectivity for clinical diagnosis of Alzheimer's disease. At the same time, the following important roles in the future will be expected.

1) Objective judgment system of effect of medicaments for treating Alzheimer's disease.

2) Detection of Alzheimer's disease before a diagnosis standard is met, or disease conditions are manifested.

Further, data obtained in different facilities can be compared with each other by using the same diagnosis marker. Therefore, development of biological diagnosis markers is recognized to be a most important field among fields of Alzheimer's disease studies and its future prospects will be expected. Approaches to development of biological diagnosis markers up to now are divided into that based on constitute components of characteristic pathological changes of Alzheimer's disease such as senile plaque and neurofibril change, and an approach based on other measures. Examples of the former include cerebrospinal fluid tau protein, Aβ and its precursor, βAPP. Examples of the latter include mydriasis test with cholilytic drug, Apo E and other genes relating to Alzheimer's disease. However, no good results are obtained.

Serine proteases are also considered to play important role in cancer cells. The reason why extermination of cancer by surgical treatment or topical irradiation of radioactive ray is difficult is metastasis capability of cancer. For spread of solid tumor cells in a body, they should loosen their adhesion to original adjacent cells, followed by separating from an original tissue, passing through other tissues to reach blood vessel or lymph node, entering into the circulatory system through stratum basal and endothelial layer of the vessel, leave from the circulatory system at somewhere in the body, and surviving and proliferating in a new environment. While adhesion to adjacent epidermal cells is lost when expression of cadherin which is an intercellular adhesive molecule of epithelium is stopped, to break through tissues is considered to depend on proteolytic enzymes which decompose an extracellular matrix.

As enzymes which decompose the matrix, mainly, metal proteases (Rha, S. Y. et al., Breast Cancer Research Treatment, 43, 175, 1997) and serine proteases are known. They cooperate to decompose matrix protein such as collagen, laminin and fibronectin. Among serine proteases known to be concerned in decomposition of the matrix, in particular, there is urokinase type plasminogen activator (U-PA). U-PA has a role as a trigger specific for a protein decomposition chain reaction. Its direct target is plasminogen. It is present in blood abundantly and is a precursor of an inactive serine protease which accumulates in reconstructed sites of tissues such as injured sites and tumors as well as inflammatory sites. In addition, as proteases which are concerned in metastasis and infiltration of cancers, for example, a tissue factor, lysosomal type hydrolase and collagenase have been known.

At present, cancer is the top cause of death in Japan and more than 200,000 people are died per year. Then, specific substances which can be used as markers for diagnosis and therapy or prophylaxis of cancer are studied intensively. Such specific substances are referred to as tumor markers or tumor marker relating biomarkers. They are utilized in aid of diagnosis before treatment of cancer, for presuming carcinogenic organ and pathological tissue type, for monitoring effect of treatment, for finding recurrence early, for presuming prognosis, and the like. At present, tumor markers are essential in clinical analyses. Among them, alpha fetoprotein (AFP) which has high specificity to hepatocellular carcinoma and yolk sac tumor (Taketa K. et al., Tumour Biol., 9, 110, 1988), and carcinoembronic antigen (CEA) are used worldwide. In the future, tumor markers will be required more and more, and it is desired to develop, for example, organ specific markers and tumor cell specific markers which are highly reliable serologic diagnosis of cancer. Up to now, humunglandular kallikrein (hK2) which is a serine protease expressed at human prostatic epithelial cells has been reported as a marker for prostatic cancer. And, hK2 has 78% homology with the sequence of prostatic specific antigen (PSA) and PSA is also used widely as a biochemical marker of prostatic cancer (Mikolajczyk, S. d. et al., Prostate, 34, 44, 1998; Pannek, J. et al., Oncology, 11, 1273, 1997; Chu, T. M. et al., Tumour Biology, 18, 123, 1997; Hsieh, M. et al., Cancer Res., 57, 2651, 1997). Further, hK2 is reported to be useful as a marker for not only prostatic cancer but also stomach cancer (Cho, J. Y. et al. Cancer, 79, 878, 1997). Moreover, CYFRA (CYFRA 21-1) for measuring cytokeratin 19 fragment in serum is reported to be useful for lung cancer (Sugiyama, Y. et al., Japan J. Cancer Res., 85, 1178, 1994). Gastrin release peptide precursor (ProGRP) is reported to be useful as a tumor marker (Yamaguchi, K. et al., Japan, J. Cancer Res., 86, 698, 1995).

OBJECTS OF THE INVENTION

Thus, the main object of the present invention is to provide a novel serine protease which can be used for treating or diagnosing various diseases such as Alzheimer's disease (AD), epilepsy, cancer, inflammation, sterility, prostate hypertrophy and the like in various tissues such as brain, lung, prostate, testicle, skeletal muscle, liver and the like, and can be used as an excellent marker instead of that presently used.

SUMMARY OF THE INVENTION

Under these circumstances, the present inventors have succeeded in cloning of cDNA encoding novel human and mouse serine proteases.

In summary, one feature of the present invention is amino acid sequences of biological active mature serine proteases hBSSP4 and mBSSP4 as well as nucleotide sequences encoding the amino acid sequences.

That is, they are the amino acid sequence composed of 268 amino acids represented by the 1st to 268th amino acids of SEQ ID NO: 2 and a nucleotide sequence encoding the amino acid sequence (the 151st to 954th bases of SEQ ID NO: 1). In addition, they include amino acid sequences substantially similar to the amino acid sequence and nucleotide sequences encoding such similar amino acid sequences. Further, they include modified derivatives of proteins having these amino acid sequences. An amino acid sequence substantially similar to a given amino acid sequence used herein means an amino acid sequence derived from the given amino acid sequence by modification such as substitution, deletion, addition and/or insertion of one to several amino acids with maintaining the same property as that of the protein having the given amino acid sequence. The modified derivative of the proteins includes, for example, phosphate adduct, sugar chain adduct, metal adduct (e.g., calcium adduct), the protein fused to another protein such as albumin etc., dimer of the protein, and the like.

Further, they are the amino acid sequence composed of 270 amino acids represented by the 1st to 270th amino acids of SEQ ID NO: 4 and a nucleotide sequence encoding the amino acid sequence (the 15th to 960th bases of SEQ ID NO: 3). In addition, they include amino acid sequences substantially similar to the amino acid sequence and nucleotide sequences encoding such similar amino acid sequences. Further, they include modified derivatives of proteins having these amino acid sequences.

Further, they are the amino acid sequence composed of 257 amino acids represented by the 1st to 257th amino acids of SEQ ID NO: 6 and a nucleotide sequence encoding the amino acid sequence (the 151st to 921st bases of SEQ ID NO: 5). In addition, they include amino acid sequences substantially similar to the amino acid sequence and nucleotide sequences encoding such similar amino acid sequences. Further, they include modified derivatives of proteins having these amino acid sequences.

Further, they are the amino acid sequence composed of 97 amino acids represented by the 1st to 97th amino acids of SEQ ID NO: 8 and a nucleotide sequence encoding the amino acid sequence (the 151st to 441st bases of SEQ ID NO: 7). In addition, they include amino acid sequences substantially similar to the amino acid sequence and nucleotide sequences encoding such similar amino acid sequences. Further, they include modified derivatives of proteins having these amino acid sequences.

Further, they are the amino acid sequence composed of 158 amino acids represented by the 1st to 158th amino acids of SEQ ID NO: 10 and a nucleotide sequence encoding the amino acid sequence (the 151st to 624th bases of SEQ ID NO: 9). In addition, they include amino acid sequences substantially similar to the amino acid sequence and nucleotide sequences encoding such similar amino acid sequences. Further, they include modified derivatives of proteins having these amino acid sequences.

Further, they are the amino acid sequence composed of 82 amino acids represented by the 1st to 82nd amino acids of SEQ ID NO: 12 and a nucleotide sequence encoding the amino acid sequence (the 151st to 396th bases of SEQ ID NO: 11). In addition, they include amino acid sequences substantially similar to the amino acid sequence and nucleotide sequences encoding such similar amino acid sequences. Further, they include modified derivatives of proteins having these amino acid sequences.

Further, they are the amino acid sequence composed of 185 amino acids represented by the 1st to 185th amino acids of SEQ ID NO: 14 and a nucleotide sequence encoding the amino acid sequence (the 151st to 705th bases of SEQ ID NO: 13). In addition, they include amino acid sequences substantially similar to the amino acid sequence and nucleotide sequences encoding such similar amino acid sequences. Further, they include modified derivatives of proteins having these amino acid sequences.

Further, they are the amino acid sequence composed of 80 amino acids represented by the 1st to 80th amino acids of SEQ ID NO: 16 and a nucleotide sequence encoding the amino acid sequence (the 151st to 390th bases of SEQ ID NO: 15). In addition, they include amino acid sequences substantially similar to the amino acid sequence and nucleotide sequences encoding such similar amino acid sequences. Further, they include modified derivatives of proteins having these amino acid sequences.

Further, they are the amino acid sequence composed of 253 amino acids represented by the 1st to 253th amino acids of SEQ ID NO: 18 and a nucleotide sequence encoding the amino acid sequence (the 151st to 909th bases of SEQ ID NO: 17). In addition, they include amino acid sequences substantially similar to the amino acid sequence and nucleotide sequences encoding such similar amino acid sequences. Further, they include modified derivatives of proteins having these amino acid sequences.

Further, they are the amino acid sequence composed of 34 amino acids represented by the -49th to -16th amino acids of SEQ ID NO: 2 and a nucleotide sequence encoding the amino acid sequence (the 4th to 105th bases of SEQ ID NO: 1). In addition, they include amino acid sequences substantially similar to the amino acid sequence and nucleotide sequences encoding such similar amino acid sequences. Further, they include modified derivatives and fragments of proteins having these amino acid sequences.

Further, they are the amino acid sequence composed of 15 amino acids represented by the -15th to -1st amino acids of SEQ ID NO: 2 and a nucleotide sequence encoding the amino acid sequence (the 106th to 150th bases of SEQ ID NO: 1). In addition, they include amino acid sequences substantially similar to the amino acid sequence and nucleotide sequences encoding such similar amino acid sequences. Further, they include modified derivatives and fragments of proteins having these amino acid sequences.

Further, they are the amino acid sequence composed of 259 amino acids represented by the 1st to 259th amino acids of SEQ ID NO: 20 and a nucleotide sequence encoding the amino acid sequence (the 227th to 1003rd bases of SEQ ID NO: 19). In addition, they include amino acid sequences substantially similar to the amino acid sequence and nucleotide sequences encoding such similar amino acid sequences. Further, they include modified derivatives of proteins having these amino acid sequences.

Further, they are the amino acid sequence composed of 34 amino acids represented by the -49th to -16th amino acids of SEQ ID NO: 20 and a nucleotide sequence encoding the amino acid sequence (the 80th to 181st bases of SEQ ID NO: 19). In addition, they include amino acid sequences substantially similar to the amino acid sequence and nucleotide sequences encoding such similar amino acid sequences. Further, they include modified derivatives and fragments of proteins having these amino acid sequences.

Further, they are the amino acid sequence composed of 15 amino acids represented by the -15th to -1st amino acids of SEQ ID NO: 20 and a nucleotide sequence encoding the amino acid sequence (the 182nd to 226th bases of SEQ ID NO: 19). In addition, they include amino acid sequences substantially similar to the amino acid sequence and nucleotide sequences encoding such similar amino acid sequences. Further, they include modified derivatives and fragments of proteins having these amino acid sequences.

Another feature of the present invention is an amino acid sequence composed of 317 or 283 amino acids wherein 49 amino acids represented by the -49th to -1st amino acids or 15 amino acids represented by the -15th to -1st amino acids of SEQ ID NO: 2 are added to the N-terminus side of the mature hBSSP4 amino acid sequence represented by SEQ ID NO: 2 (the 1st to 268th amino acids) and a nucleotide sequence encoding the amino acid sequence (the 4th to 954th or 106th to 954th bases of SEQ ID NO: 1). In addition, this feature includes amino acid sequences substantially similar to the above amino acid sequence and nucleotide sequences encoding these substantially similar amino acid sequences. Further, this feature includes modified derivatives of proteins having these amino acid sequences.

Another feature of the present invention is an amino acid sequence composed of 319 or 285 amino acids wherein 49 amino acids represented by the -49th to -1st amino acids or 15 amino acids represented by the -15th to -1st amino acids of SEQ ID NO: 4 are added to the N-terminus side of the mature hBSSP4 amino acid sequence represented by SEQ ID NO: 4 (the 1st to 270th amino acids) and a nucleotide sequence encoding the amino acid sequence (the 4th to 960th or 106th to 960th bases of SEQ ID NO: 3). In addition, this feature includes amino acid sequences substantially similar to the above amino acid sequence and nucleotide sequences encoding these substantially similar amino acid sequences. Further, this feature includes modified derivatives of proteins having these amino acid sequences.

Another feature of the present invention is an amino acid sequence composed of 306 or 272 amino acids wherein 49 amino acids represented by the -49th to -1st amino acids or 15 amino acids represented by the -15th to -1st amino acids of SEQ ID NO: 6 are added to the N-terminus side of the mature hBSSP4 amino acid sequence represented by SEQ ID NO: 6 (the 1st to 257th amino acids) and a nucleotide sequence encoding the amino acid sequence (the 4th to 921st or 106th to 921st bases of SEQ ID NO: 5). In addition, this feature includes amino acid sequences substantially similar to the above amino acid sequence and nucleotide sequences encoding these substantially similar amino acid sequences. Further, this feature includes modified derivatives of proteins having these amino acid sequences.

Another feature of the present invention is an amino acid sequence composed of 308 or 274 amino acids wherein 49 amino acids represented by the -49th to -1st amino acids or 15 amino acids represented by the -15th to -1st amino acids of SEQ ID NO: 20 are added to the N-terminus side of the mature mBSSP4 amino acid sequence represented by SEQ ID NO: 20 (the 1st to 259th amino acids) and a nucleotide sequence encoding the amino acid sequence (the 8th to 1003rd or 182nd to 1003rd bases of SEQ ID NO: 19). In addition, this feature includes amino acid sequences substantially similar to the above amino acid sequence and nucleotide sequences encoding these substantially similar amino acid sequences. Further, this feature includes modified derivatives of proteins having these amino acid sequences.

The present invention also relates to the nucleotide sequences represented by SEQ ID NOS: 1, 3, 5, 7, 9, 11, 13, 15, 17 and 19 as well as nucleotide sequences similar to them.

Hereinafter, unless otherwise stated, the nucleotide sequence represented by each SEQ ID NO: includes the above-described various fragments thereof, and similar nucleotide sequences and their fragments. Likewise, the amino acid sequence represented by each SEQ ID NO: includes the above-described various fragments thereof, similar nucleotide sequences and their fragments, and modified derivatives thereof. In addition, unless otherwise stated, BSSP4, hBSSP4, and mBSSP4 include proteins having the above-described respective amino acid sequences.

DETAILED DESCRIPTION OF THE INVENTION

Figure 1:
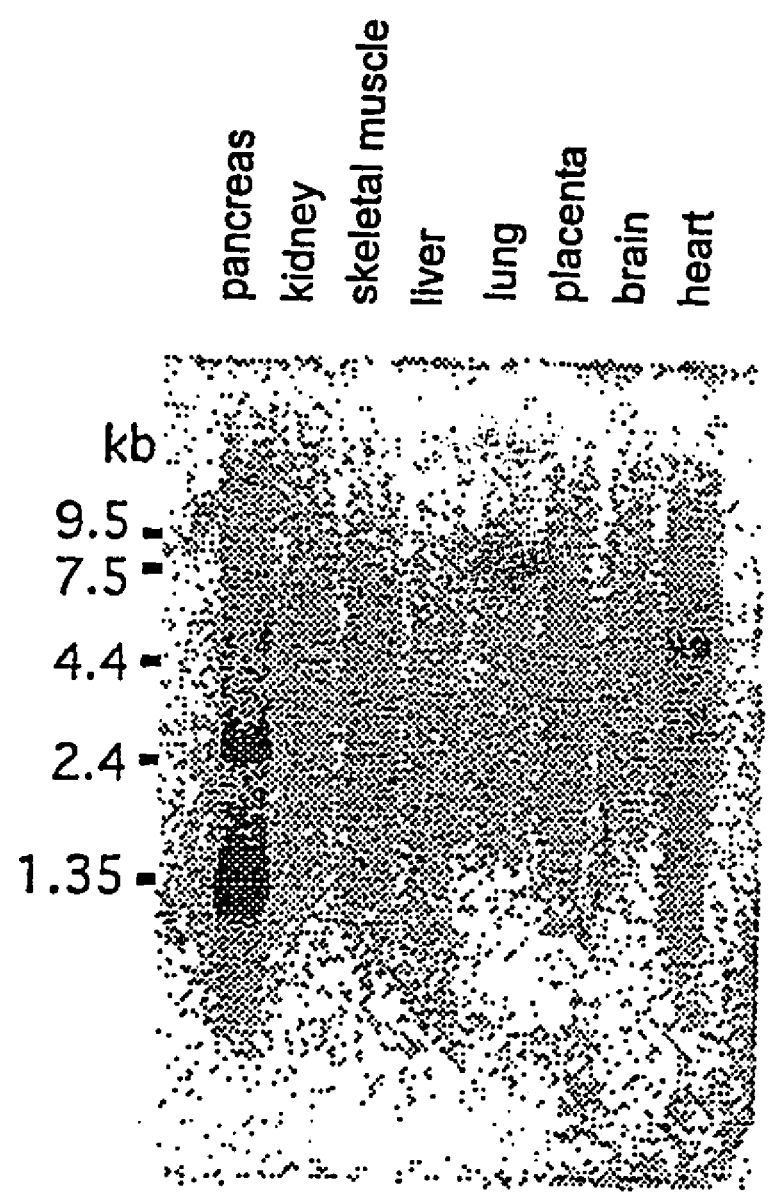
FIG. 1 illustrates the results of northern blotting using human multiple tissue blot membrane.

The nucleotide sequences encoding hBSSP4 or mBSSP4 of the present invention can be obtained by preparing mRNAs from cells expressing the protein and converting it into double stranded DNAs according to a conventional manner. For preparing mRNA, guanidine isothiocyanate-calcium chloride method (Chirwin, et al., Biochemistry, 18, 5294, 1979) or the like can be used. For preparing poly (A)+RNA from total RNAs, there can be used affinity chromatography using a carrier, for example, Sepharose, latex particles, etc., to which oligo (dT) is attached, and the like. The above-obtained RNA can be used as a template and treated with reverse transcriptase by using, as a primer, oligo (dT) which is complementary to the poly (A) strand at the 3'-terminus, or a random primer, or a synthesized oligonucleotide corresponding to a part of the amino acid sequence of hBSSP4 or mBSSP4 to obtain a hybrid mRNA strand comprising DNA complementary to the mRNA or cDNA. The double stranded DNA can be obtained by treating the above-obtained hybrid mRNA strand with *E. coli* RNase, *E. coli* DNA polymerase and *E. coli* DNA ligase to convert into a DNA strand.

It is also possible to carry out cloning by RT-PCR method using primers synthesized on the basis of the nucleotide sequence of hBSSP4 or mBSSP4 gene and using hBSSP4 or mBSSP4 expressing cell poly (A)+RNA as a template. Alternatively, the desired cDNA can be obtained without using PCR by preparing or synthesizing a probe on the basis of the nucleotide sequence of hBSSP4 or mBSSP4 gene and screening a cDNA library directly. Among genes obtained by these methods, the gene of the present invention can be selected by confirming a nucleotide sequence thereof. The gene of the present invention can also be prepared according to a conventional method using chemical syntheses of nucleic acids, for example, phosphoamidite method (Mattencci, M. D. et al., J. Am. Chem. Soc., 130, 3185, 1981) and the like.

By using the thus-obtained hBSSP4 or mBSSP4 gene, their expression in various tissues can be examined.

In case of northern blotting analysis, the expression of hBSSP4 is observed in cerebellum and prostate, and the expression of mBSSP4 is observed in prostate and skeletal muscle. In case of RT-PCR analysis, the expression of hBSSP4 is observed in brain, placenta and prostate of human fetuses and adults and the expression of mBSSP4 is observed in brain and placenta of 12-day-old mice. Then, the novel proteases of the present invention are presumed to play various roles in brain, prostate, placenta and skeletal muscle. For example, in brain, there is a possibility that they can be used for treatment and diagnosis of brain diseases such as Alzheimer's disease (AD), epilepsy, brain tumor and the like. Further, in other tissues, there is a possibility that they can be used for treatment and diagnosis of various diseases such as cancer, inflammation, sterility, prostate hypertrophy and the like. Further, it is presumed they may have a certain influence on blood coagulation, fibrinolysis and complement systems.

The human novel serine protease (hBSSP4) is composes of 9 proteins due to alternative splicing of mRNA.

The protein having the amino acid sequence represented by SEQ ID NO: 2 is a human type protein (hBSSP4) and the mature type having serine protease activity is the polypeptide represented by the 1st to 268th amino acids. As consensus sequences of serine proteases, it has Ala-Ala-His-Cys corresponding to the 39th to 42nd amino acid residues of SEQ ID NO:2 and Asp-Ser-Gly-Gly-Pro corresponding to the 192nd to 196th amino acid residues of SEQ ID NO:2 and one or more of Asp's are present between the concensus sequences. A nucleotide sequence encoding this protein is shown in SEQ ID NO:1.

The protein having the amino acid sequence represented by SEQ ID NO:4 is a human type protein (hBSSP4) and the mature type having serine protease activity is the polypeptide represented by the 1st to 270th amino acids. As consensus sequences of serine proteases, it has Ala-Ala-His-Cys corresponding to residues of the 39th to 42nd amino acids of SEQ ID NO:4 and Asp-Ser-Gly-Gly-Pro corresponding to residues of the represented by the 192nd to 196th amino acids of SEQ ID NO:1 and one or more of Asp's are present between the concensus sequences. A nucleotide sequence encoding this protein is shown in SEQ ID NO:3. This sequence corresponds to SEQ ID NO:1 from which the 943rd to 1217th bases have been removed, and the amino acid sequence represented by SEQ ID NO:4 corresponds to the amino acid sequence represented by SEQ ID NO:2 in which the 265th amino acid and the subsequent amino acids are different.

The protein having the amino acid sequence represented by SEQ ID NO:6 is a human type protein (hBSSP4) and the mature type having serine protease activity is the polypeptide represented by the 1st to 257th amino acids. As consensus sequences of serine proteases, it has Ala-Ala-His-Cys corresponding to the 39th to 42nd amino acid residues of SEQ ID NO:6 and Asp-Ser-Gly-Gly-Pro corresponding to the 192nd to 196th amino acid residues of SEQ ID NO:2 and one or more of Asp's are present between the concensus sequences. A nucleotide sequence encoding this protein is shown in SEQ ID NO:5. This sequence corresponds to SEQ ID NO:1 from which the 895th to 11208th bases have been removed, and the amino acid sequence represented by SEQ ID NO:6 correspond to the amino acid sequence represented by SEQ ID NO:2 in which the 249th amino acids and the subsequnent amino acids are different. Further, the nucleotide sequence corresponds to the sequence wherein the 969th to 1036th bases of SEQ ID NO:5 are added to the downstream of the 1282 base of SEQ ID NO:1.

The protein having the amino acid sequence represented by SEQ ID NO: 8 is a human type protein (hBSSP4). However, it does not have a consensus sequence of serine proteases. Since its expression by mRNA has been confirmed, this sequence is consiered to have a certain role. The nucleotide sequence corresponds to the nucleotide sequence of SEQ ID NO: 1 from which the 233rd to 282nd bases have been removed.

The protein having the amino acid sequence represented by SEQ ID NO: 10 is a human type protein (hBSSP4). As a consensus sequence of serine proteases, this does not have Ala-Ala-His-Cys corresponding to the 39th to 42nd amino acid residues of SEQ ID NO:10, but has Asp-Ser-Gly-Gly-Pro corresponding to residues of the 82nd to 86th amino acids of SEQ ID NO:10. A nucleotide sequence encoding this protein is shown in SEQ ID NO:9. This sequence corresponds to the nucleotide sequence of SEQ ID NO:1 from which the 233rd to 562nd bases have been removed.

The protein having the amino acid sequence represented by SEQ ID NO: 12 is a human type protein (hBSSP4). As a consensus sequence of serine proteases, it has Ala-Ala-His-Cys corresponding to residues 39th to 42nd amino acids of SEQ ID NO:12 but does not have Asp-Ser-Gly-Gly-Pro corresponding to residues of the 82nd to 86th amino acids of SEQ ID NO:10. A nucleotide sequence encoding this protein is shown in SEQ ID NO:11. This nucleotide sequence corresponds to the nucleotide sequence represented by SEQ ID NO:1 from which the 364th to 562nd amino acids have been removed.

The protein having the amino acid sequence represented by SEQ ID NO:14 is a human type protein (hBSSP4). As a consensus sequence of serine proteases, it has Ala-Ala-His-Cys corresponding to the 39th to 42nd amino acid residues of SEQ ID NO:14 but do not have Asp-Ser-Gly-Gly-Pro corresponding to residues of the $82^{nd}$ to 86ht amino acid of SEQ ID NO:10. A nucleotide sequence encoding this protein is shown in SEQ ID NO:13. This nucleotide sequence corresponds to the nucleotide sequence represented by SEQ ID NO:1 from which the 588th to 1145th bases have been removed. There is a possibility that the nucleotide sequence represented by the 652nd and the subsequent bases of SEQ ID NO: 13 would be "ccc ggg ccc cag cgc ttt tgt gta tat aaa tgt taatgatttt tataggtatt tgtaaccctg cccacatatc" SEQ ID NO:49 and the amino acid sequence represented by the 168th and the subsequent amino acids of SEQ ID NO: 14 would be "Pro Gly Pro Gln Arg Phe Cys Val, Tyr Lys Cys" SEQ ID NO:50.

The protein having the amino acid sequence represented by SEQ ID NO:16 is a human type protein (hBSSP4). As a consensus sequence of serine proteases, it has Ala-Ala-His-Cys corresponding to the 39th to 42nd amino acid residues of SEQ ID NO:16 but does not have Asp-Ser-Gly-Gly-Pro corresponding to the 82nd to 86th amino acid residues of SEQ ID NO:10. A nucleotide sequence encoding this protein is shown in SEQ ID NO:15. This sequence corresponds to SEQ ID NO: 1 from which the 285th to 562nd bases have been removed.

The protein having the amino acid sequence represented by SEQ ID NO: 18 is a human type protein (hBSSP4). As a consensus sequence of serine proteases, it has Ala-Ala-His-Cys corresponding to the 39th to 42nd amino acid residues of SEQ ID NO:18 but does not have Asp-Ser-Gly-Gly-Pro corresponding to the 82nd to 86th amino acid residues of SEQ ID NO:10. A nucleotide sequence encoding this protein is shown in SEQ ID NO:17. This sequence corresponds to the sequence wherein the 721st to 948th bases of SEQ ID NO: 17 is added to the downstream of the 720th base of SEQ ID NO: 1, and corresponds SEQ ID NO:1 from which the 720th and the subsequent bases have been removed. The protein having the amino acid sequence represented by SEQ ID NO:20 is a mouse type protein (mBSSP4) and the mature type having serine protease activity is the polypeptide represented by the 1st to 253 amino acids. As consensus sequences of serine proteases, it has Ala-Ala-His-Cys corresponding to the 39th to 42nd amino acid residues of SEQ ID NO:20 and Asp-Ser-Gly-Gly-Pro corresponding to the 192nd to 196th amino acid residues of SEQ ID NO:20 and one or more of Asp's are present between the concensus sequences. A nucleotide sequence encoding this protein is shown in SEQ ID NO: 19.

The term "pro part" used herein means a part of a pro-form, i.e., the pro-form from which the corresponding active type protein part is removed. The term "pre part" used herein means a part of a prepro-form, i.e., the prepro-form from which the corresponding pro-form is removed. The term "prepro part" used herein means a part of a prepro-form, i.e., the prepro-form from which the corresponding active type protein part is removed.

The amino acid sequence of mature hBSSP4 (the 1st to 268th amino acids) represented by SEQ ID NO: 2 is hBSSP4 mature or active type protein composed of 268 amino acids, and the nucleotide sequence encoding the amino acid sequence is composed of 804 bases. The present inventors have shown that the serine protease activity is maintained even when one to several amino acids of the N-terminus of the mature type protein of the present invention is deleted or added, while the preferred sequence is this amino acid sequence. The sequence of the -49th to -1st amino acids is the prepro or pro part and the amino acid sequence of the -15th to -1st amino acids is the pro part and is considered to be a precursor of hBSSP4 protein.

The amino acid sequence of mature hBSSP4 (the 1st to 270th amino acids) represented by SEQ ID NO: 4 is hBSSP4 mature or active type protein composed of 270 amino acids, and the nucleotide sequence encoding the amino acid sequence is composed of 810 bases. The present inventors have shown that the serine protease activity is maintained even when one to several amino acids of the N-terminus of the mature type protein of the present invention is deleted or added, while the preferred sequence is this amino acid sequence. The sequence of the -49th to -1st amino acids is the prepro or pro part and the amino acid sequence of the -15th to -1st amino acids is the pro part and is considered to be a precursor of hBSSP4 protein.

The amino acid sequence of mature hBSSP4 (the 1st to 257th amino acids) represented by SEQ ID NO: 6 is hBSSP4 mature or active type protein composed of 257 amino acids, and the nucleotide sequence encoding the amino acid sequence is composed of 771 bases. The present inventors have shown that the serine protease activity is maintained even when one to several amino acids of the N-terminus of the mature type protein of the present invention is deleted or added, while the preferred sequence is this amino acid sequence. The sequence of the -49th to -1st amino acids is the prepro or pro part and the amino acid sequence of the -15th to -1st amino acids is the pro part and is considered to be a precursor of hBSSP4 protein.

The amino acid sequence of hBSSP4 (the 1st to 97th amino acids) represented by SEQ ID NO: 8 is a protein composed of 97 amino acids, and the nucleotide sequence encoding the amino acid sequence is composed of 291 bases. The sequence of the -49th to -1st amino acids is the prepro or pro part and the amino acid sequence of the -15th to -1st amino acids is the pro part and is considered to be a precursor of hBSSP4 protein.

The amino acid sequence of hBSSP4 (the 1st to 158th amino acids) represented by SEQ ID NO: 10 is a protein composed of 158 amino acids, and the nucleotide sequence encoding the amino acid sequence is composed of 474 bases. The sequence of the -49th to -1st amino acids is the prepro or pro part and the amino acid sequence of the -15th to -1st amino acids is the pro part and is considered to be a precursor of hBSSP4 protein.

The amino acid sequence of hBSSP4 (the 1st to 82nd amino acids) represented by SEQ ID NO: 12 is a protein composed of 82 amino acids, and the nucleotide sequence encoding the amino acid sequence is composed of 246 bases. The sequence of the -49th to -1st amino acids is the prepro or pro part and the amino acid sequence of the -15th to -1st amino acids is the pro part and is considered to be a precursor of hBSSP4 protein.

The amino acid sequence of hBSSP4 (the 1st to 185th amino acids) represented by SEQ ID NO: 14 is a protein composed of 185 amino acids, and the nucleotide sequence encoding the amino acid sequence is composed of 555 bases. The sequence of the -49th to -1st amino acids is the prepro or pro part and the amino acid sequence of the -15th to -1st amino acids is the pro part and is considered to be a precursor of hBSSP4 protein.

The amino acid sequence of hBSSP4 (the 1st to 80th amino acids) represented by SEQ ID NO: 16 is a protein composed of 80 amino acids, and the nucleotide sequence encoding the amino acid sequence is composed of 240 bases. The sequence of the -49th to -1st amino acids is the prepro or pro part and the amino acid sequence of the -15th to -1st amino acids is the pro part and is considered to be a precursor of hBSSP4 protein.

The amino acid sequence of hBSSP4 (the 1st to 253th amino acids) represented by SEQ ID NO: 18 is a protein composed of 253 amino acids, and the nucleotide sequence encoding the amino acid sequence is composed of 759 bases. The sequence of the -49th to -1st amino acids is the prepro or pro part and the amino acid sequence of the -15th to -1st amino acids is the pro part and is considered to be a precursor of hBSSP4 protein.

The amino acid sequence of mature mBSSP4 (the 1st to 259th amino acids) represented by SEQ ID NO: 20 is hBSSP4 mature or active type protein composed of 259 amino acids, and the nucleotide sequence encoding the amino acid sequence is composed of 777 bases. The present inventors have shown that the serine protease activity is maintained even when one to several amino acids of the N-terminus of the mature type protein of the present invention is deleted or added, while the preferred sequence is this amino acid sequence. The sequence of the -49th to -1st amino acids is the prepro or pro part and the amino acid sequence of the -15th to -1st amino acids is the pro part and is considered to be a precursor of mBSSP4 protein.

In general, many genes of eucaryote exhibit polymorphism and, sometimes, one or more amino acids are substituted by this phenomenon. Further, even in such case, sometimes, a protein maintains its activity. Then, the present invention includes a gene encoding a protein obtained by modifying a gene encoding any one of the amino acid sequences represented by SEQ ID NOS: 2, 4, 6, 8, 10, 12, 14, 16, 18 and 20, artificially, in so far as the protein has the characteristic function of the gene of the present invention. Further, the present invention includes a protein which is a modification of any one of amino acid sequences represented by SEQ ID NOS: 2, 4, 6, 8, 10, 12, 14, 16, 18 and 20 in so far as the protein has the characteristics of the present invention. Modification is understood to include substitution, deletion, addition and/or insertion. In particular, the present inventors have shown that, even when several amino acids are added to or deleted from the N-terminus amino acid of the hBSSP4 or mBSSP4 mature protein represented by SEQ ID NO: 2, 4, 6 or 20, the resultant sequence maintains its activity.

That is, the present invention includes a protein comprising any one of amino acid sequences described in SEQ ID NOS: 2, 4, 6, 8, 10, 12, 14, 16, 18 and 20; an amino acid sequence encoded by any one of nucleotide sequences represented by SEQ ID NOS: 1, 3, 5, 7, 9, 11, 13, 15, 17 and 19; or one of these amino acid sequences wherein one to several amino acids have been substituted, deleted, added and/or inserted, and being belonging to serine protease family.

Each codon for the desired amino acid itself has been known and it can be selected freely. For example, codons can be determined according to a conventional manner by taking into consideration of frequency of use of codons in a host to be utilized (Grantham, R. et al., Nucleic Acids Res., 9, r43, 1989). Therefore, the present invention also includes a nucleotide sequence appropriately modified by taking into consideration of degeneracy of a codon. Further, these nucleotide sequences can be modified by a site directed mutagenesis using a primer composed of a synthetic oligonucleotide encoding the desired modification (Mark, D. F. et al., Proc. Natl. Acad. Sci. USA., 81, 5662, 1984), or the like.

Furthermore, the DNA of the present invention includes DNA which is hybridizable to any one of nucleotide sequences described in SEQ ID NOS: 1, 3, 5, 7, 9, 11, 13, 15, 17 and 19 or nucleotide sequences complementary to these nucleotide sequences in so far as the protein encoded by the nucleotide sequence has the same properties as those of hBSSP4 or mBSSP4 of the present invention. It is considered that many of sequences which are hybridizable to a given sequence under stringent conditions have a similar activity to that of a protein encoded by the given sequence. The stringent conditions according to the present invention includes, for example, incubation in a solution containing 5×SSC, 5% Denhardt's solution (0.1% BSA, 0.1% Ficol 1400, 0.1% PVP), 0.5% SDS and 20 µg/ml denatured salmon sperm DNA at 37° C. overnight, followed by washing with 2×SSC containing 0.1% SDS at room temperature. Instead of SSC, SSPE can be appropriately used.

Probes for detecting a hBSSP4 or mBSSP4 gene can be designed based on any one of nucleotide sequences described in SEQ ID NOS: 1, 3, 5, 7, 9, 11, 13, 15, 17 and 19. Or, primers can be designed for amplifying DNA or RNA containing the nucleotide sequence. To design probes or primers is carried out routinely by a person skilled in the art. An oligonucleotide having a designed nucleotide sequence can be synthesized chemically. And, when a suitable label is added to the oligonucleotide, the resultant oligonucleotide can be utilized in various hybridization assay. Or, it can be utilized in nucleic acid synthesis reactions such as PCR. An oligonucleotide to be utilized as a primer has, preferably, at least 10 bases, more preferably 15 to 50 bases in length. An oligonucleotide to be utilized as a probe has, preferably, 100 bases to full length.

Moreover, it is possible to obtain a promoter region and an enhancer region of a hBSSP4 or mBSSP4 gene present in the genome based on the cDNA nucleotide sequence of hBSSP4 or mBSSP4 provided by the present invention. Specifically, these control regions can be obtained according to the same manner as described in JP 6-181767 A; J. Immunol., 155, 2477, 1995; Proc. Natl. Acad. Sci., USA, 92, 3561, 1995 and the like. The promoter region used herein means a DNA region which is present upstream from a transcription initiation site and controls expression of a gene. The enhancer region used herein means a DNA region which is present in an intron, a 5'-non-translated region or a 3'-non-translated region and enhances expression of a gene.

The present invention also relates to a vector comprising the nucleotide sequence represented by SEQ ID NO: 1, 3, 5, 7, 9, 11, 13, 15, 17 or 19, or a nucleotide sequence encoding the amino acid sequence represented by SEQ ID NO: 2, 4, 6, 8, 10, 12, 14, 16, 18 ir 20, or a nucleotide sequence similar to these sequences. A nucleotide sequence similar to a give nucleotide sequence used herein means a nucleotide sequence which is hybridizable to the given nucleotide sequence or its complementary nucleotide sequence under the above-described stringent conditions and encodes a protein having the same properties as those of the protein encoded by the nucleotide sequence.

The vector is not specifically limited in so far as it can express the protein of the present invention. Examples thereof include pBAD/His, pRSETA, pcDNA2.1, pTrcHis2A, pYES2, pBlueBac4.5, pcDNA3.1 and pSecTag2 manufacture by Invitrogen, pET and pBAC manufactured by Novagen, pGEM manufactured by Promega, pBluescriptII manufactured by Stratagene, pGEX and pUC18/19 manufactured by Pharmacia, PfastBAC1 manufactured by GIBCO and the like. Preferably, a protein expression vector (described in the specification of a patent application entitled "Protein expression vector and its use" and filed by the same applicant on the same day) is used. This expression vector is constructed by using pCRII-TOPO vector described in the Examples hereinafter, or a commercially available expression vector, for example pSecTag2A vector or pSecTag2B vector (Invitrogen) and integrating a secretory signal nucleotide sequence suitable for expression of the protein of the present invention, in the 3' downstream side thereof, a Tag nucleotide sequence, a cleavable nucleotide sequence and a cloning site, into which a nucleotide sequence encoding a target protein can be inserted, in this order. More specifically, it is preferred to use trypsin signal as the secretory signal, a nucleotide sequence encoding polyhistidine as the Tag nucleotide sequence, and a nucleotide sequence encoding an amino acid sequence which is susceptible to enzyme-specific cleavage, i.e., a nucleotide sequence encoding the amino acid sequence of Asp-Asp-Asp-Asp-Lys SEQ ID NO:51 (said amino acid sequence is recognized by enterokinase, and the recombinant fusion protein is cleaved at the C-terminus part thereof) as the cleavable nucleotide sequence.

Furthermore, the present invention provides transformed cells having the nucleotide sequence of the present invention in an expressible state by means of the above vector. Preferably, host cells to be used for the transformed cells of the present invention are animal cells and insect cells. However, host cells include any cells (including those of microorganisms) which can express a nucleotide sequence encoding the desired protein in the expression vector of the present invention and can secrete extracellularly.

The animal cells and insect cells used herein include cells derived from human being and cells derived from fly or silk worm. For example, there are CHO cell, COS cell, BHK cell, Vero cell, myeloma cell, HEK293 cell, HeLa cell, Jurkat cell, mouse L cell, mouse C127 cell, mouse FM3A cell, mouse fibroblast, osteoblast, cartilage cell, S2, Sf9, Sf21, High Five™ (registered trade mark) cell and the like. The microorganisms used herein include *E. coli* and yeast.

The protein of the present invention as such can be expressed as a recombinant fused protein so as to facilitate isolation, purification and recognition. The recombinant fused protein used herein means a protein expressed as an adduct wherein a suitable peptide chain are added to the N-terminus and/or C-terminus of the desired protein expressed by a nucleotide sequence encoding the desired protein. The recombinant protein used herein means that obtained by integrating a nucleotide sequence encoding the desired protein in the expression vector of the present invention and cut off an amino acid sequence which derived from nucleic acids other than those encoding the desired protein from the expressed recombinant fused protein, and is substantially the same as the protein of the present invention.

Introduction of the above vector into host cells can be carried out by, for example, transfection according to lipopolyamine method, DEAE-dextran method, Hanahan method, lipofectin method or calcium phosphate method, microinjection, eletroporation and the like.

As described above, the present invention also relates to a process for producing hBSSP4 of mBSSP4 comprising culturing cells transformed with the above nucleotide sequence of the present invention and collecting the produced hBSSP4 of mBSSP4. The culture of cells and separation and purification of the protein can be carried out by a per se known method.

The present invention also relates to an inhibitor of the novel serine protease of the present invention. Screening of the inhibitor can be carried out according to a per se known method such as comparing the enzyme activity upon bringing into contact with a candidate compound with that without contact with the candidate compound, or the like The present invention relates to a non-human transgenic animal whose expression level of hBSSP4 or mBSSP4 gene has been altered. The hBSSP4 or mBSSP4 gene used herein includes cDNA, genomic DNA or synthetic DNA encoding hBSSP4 or mBSSP4. In addition, expression of a gene includes any steps of transcription and translation. The non-human transgenic animal of the present invention is useful for studies of functions or expression control of hBSSP4 or mBSSP4, elucidation of mechanisms of diseases in which hBSSP4 or mBSSP4 is presumed to be involved, and development of disease model animals for screening and safety test of medicine.

In the present invention, expression of a gene can be modified artificially by mutagenizing at a part of several important sites which control normal gene expression (enhancer, promoter, intron, etc.) such as deletion, substitution, addition and/or insertion to increase or decrease an expression level of the gene in comparison with its inherent expression level. This mutagenesis can be carried out according to a known method to obtain the transgenic animal.

In a narrow sense, the transgenic animal means an animal wherein a foreign gene is artificially introduced into reproductive cells by gene recombinant techniques. In a broad sense, the transgenic animal includes an antisense transgenic animal of whose function a specific gene is inhibited by using antisense RNA, an animal whose specific gene is knocked out by using embryonic stem cells (ES cells), and an animal into which point mutation DNA is introduced, and the transgenic animal means an animal into which a foreign gene is stably introduced into a chromosome at an initial stage of ontogeny and the genetic character can be transmitted to the progeny.

The transgenic animal used herein should be understood in a broad sense and includes any vertebrates other than a human being. The transgenic animal of the present invention is useful for studies of functions or expression control of hBSSP4 or mBSSP4, elucidation of mechanisms of diseases associated with cells expressing in a human being, and development of disease model animals for screening and safety test of medicine.

As a technique for creating the transgenic animal, a gene is introduced into a nucleus in a pronucleus stage of egg cells with a micropipette directly under a phase-contrast microscope (microinjection, U.S. Pat. No. 4,873,191). Further, there are a method using embryonic stem cell (ES cell), and the like. In addition, there are newly developed methods such as a method wherein a gene is introduced into a retroviral vector or adenoviral vector to infect egg cells, a sperm vector method wherein a gene is introduced into egg cells through sperms, and the like.

A sperm vector method is a gene recombinant technique wherein a foreign gene is incorporated into sperm cells by adhesion, electroporation, etc., followed by fertilization of egg cells to introduce the foreign gene into the egg cells (M. Lavitranoet et al., Cell, 57, 717, 1989). Alternatively, an in vivo site specific gene recombinant technique such as that using cre/loxP recombinase system of bacteriophage P1, FLP recombinase system of *Saccharomyces cerevisiae*, etc. can be used. Furthermore, introduction of a transgene of the desired protein into a non-human animal using a retroviral vector has been reported.

For example, a method for creating a transgenic animal by microinjection can be carried out as follows.

First, a transgene primarily composed of a promoter responsible for expression control, a gene encoding a specific protein and a poly A signal is required. It is necessary to confirm expression modes and amounts between respective systems because an expression mode and amount of a specific molecule is influenced by a promoter activity, and transgenic animals differ from each other according to a particular system due to the difference in a copy number of an introduced transgene and a introduction site on a chromosome. An intron sequence which is spliced may be previously introduced before the poly A signal because it has been found that an expression amount varies due to a non-translation region and splicing. Purity of a gene to be used for introduction into fertilized egg cells should be as high as possible. This is of importance. Animals to be used include a mouse for collecting fertilized eggs (5 to 6 week old), a male mouse for mating, a false pregnancy female mouse, a seminiferous tubule-ligated mouse, and the like.

For obtaining fertilized egg cells efficiently, ovulation may be induced with gonadotropin or the like. Fertilized egg cells are recovered and a gene in an injection pipette is injected into male pronucleus of the egg cells by microinjection. For returning the injected egg cells to a fallopian tube, an animal (false pregnancy female mouse, etc.) is provided and about 10 to 15 eggs/mouse are transplanted. Then, genomic DNA is extracted from the end part of the tail to confirm whether the transgene is introduced into newborn mouse or not. This confirmation can be carried out by detection of the transgene with southern blot technique or PCR technique, or by positive cloning wherein a marker gene, which is activated only when homologous recombination is caused, has been introduced. Further, transcribed products derived from the transgene are detected by northern blot technique or RT-PCR technique to confirm expression of the transgene. Or, western blotting can be carried out with a specific antibody to a protein.

The knockout mouse of the present invention is treated so that the function of mBSSP4 gene is lost. A knockout mouse means a transgenic mouse any of whose gene is destroyed by homologous recombination technique so that its function is deficient. A knockout mouse can be created by carrying out homologous recombination with ES cells and selecting embryonic stem cells wherein either of allele genes are modified or destroyed. For example, embryonic stem cells whose genes are manipulated at blastocyte or morula stage of fertilized eggs are injected to obtain a chimera mouse wherein cells derived from the embryonic stem cells are mixed with those derived from the embryo. The chimera mouse (chimera means a single individual formed by somatic cells based on two or more fertilized eggs) can be mated with a normal mouse to create a heterozygote mouse wherein all of either of the allele genes have been modified or destroyed. Further, a homozygote mouse can be created by mating heterozygote mice.

Homologous recombination means recombination between two genes whose nucleotide sequences are the same or very similar to each other in terms of gene recombination mechanism. PCR can be employed to select homologous recombinant cells. A PCR reaction can be carried out by using a part of a gene to be inserted and a part of a region where the insertion is expected as primers to find out occurrence of homologous recombination in cells which give an amplification product. Further, for causing homologous recombination in a gene expressed in embryonic stem cells, homologous recombinant cells can readily be selected by using a known method or its modification. For example, cells can be selected by joining a neomycin resistant gene to a gene to be introduced to impart neomycin resistance to cells after introduction.

The present invention also provide an antibody recognizing hBSSP4 or mBSSP4 or a fragment thereof. The antibody of the present invention includes an antibody against a protein having the amino acid sequence described in any of SEQ ID NOS: 2, 4, 6, 18 and 20 or its fragment. An antibody against hBSSP4 or mBSSP4 or a fragment thereof (e.g., polyclonal antibody, monoclonal antibody, peptide antibody) or an antiserum can be produced by using hBSSP4 or mBSSP4 or a fragment thereof, etc. as an antigen according to a per se known process for producing an antibody or an antiserum.

The hBSSP4 or mBSSP4 or a fragment thereof is administered to a site of a warm-blooded animal where an antibody can be produced by administration thereof as such or together with a diluent or carrier. For enhancing the antibody production, upon administration, Freund's complete adjuvant or Freund's incomplete adjuvant may be administrated. Normally, the administration is carried out once every 1 to 6 weeks, 2 to 10 times in all. Examples of the warm-blooded to be used include monkey, rabbit, dog, guinea pig, mouse, rat, sheep, goat, chicken and the like with mouse and rat being preferred. As rats, for example, Wistar and SD rats are preferred. As mice, for example, BALB/c, C57BL/6 and ICR mice are preferred.

For producing monoclonal antibody producer cells, individuals whose antibody titer have been recognized are selected from warm-blooded animals, e.g., a mouse immunized with an antigen. Two to 5 days after the last immunization, the spleen or lymph node of the immunized animal is collected and antibody producer cells contained therein are subjected to cell fusion with myeloma cells to prepare a monoclonal antibody producer hybridoma. The antibody titer in an antiserum can be determined by, for example, reacting the antiserum with a labeled hBSSP4 or mBSSP4 as described hereinafter, followed by measurement of the activity bound to the antibody. The cell fusion can be carried out according to a known method, for example, that described by Koehler and Milstein (Nature, 256, 495, 1975) or its modifications (J. Immunol. Method, 39, 285, 1980; Eur. J. biochem, 118, 437, 1981; Nature, 285, 446, 1980). As a fusion promoting agent, there are polyethylene glycol (PEG), Sendai virus and the like. Preferably, PEG is used. Further, for improving fusion efficiency, lectin, poly-L-lysine or DMSO can be appropriately added.

Examples of myeloma cells include X-63Ag8, NS-1, P3U1, SP2/0, AP-1 and the like with SP2/0 being preferred. The preferred ratio of the number of the antibody producer cells (spleen cells): the number of spleen cells are 1:20 to 20:1. PEG (preferably PEG 1000 to PEG 6000) is added at a concentration of about 10 to 80% and the mixture is incubated at 20 to 40° C., preferably 30 to 37° C. for 1 to 10 minutes to carry out the cell fusion efficiently. Screening of anti-hBSSP4 or mBSSP4 antibody producer hybridomas can be carried out by various methods. For example, a supernatant of a hybridoma culture is added to a solid phase to which hBSSP4 or mBSSP4 antigen is adsorbed directly or together with a carrier (e.g., microplate), followed by addition of an anti-immunoglobulin antibody (in case that the cells used in cell fusion is those of a mouse, anti-mouse immunoglobulin antibody is used) or protein A to detect the anti-hBSSP4 or mBSSP4 monoclonal antibody attached to the solid phase. Or, a supernatant of a hybridoma culture is added to a solid phase to which an anti-immunoglobulin antibody or protein A is adsorbed, followed by addition of hBSSP4 or mBSSP4 labeled with a radioactive substance, an enzyme, etc., to detect the anti-hBSSP4 or mBSSP4 monoclonal antibody attached to the solid phase.

Selection and cloning of the anti-hBSSP or mBSSP monoclonal antibody can be carried out according to a per se known method or its modification. Normally, a HAT (hypoxanthine, aminopterin, thymidine)-added medium for culturing animal cells is used. Any culture medium can be used for selection, cloning and growing up in so far as the hybridoma can grow. For example, there can be used RPMI culture medium containing 1 to 20%, preferably 10 to 20% fetal bovine serum, or a serum-free medium for culturing hybridomas. Preferably, the culture is carried out at a temperature of about 37° C. Normally, the culture time is 5 days to 3 weeks, preferably 1 weeks to 2 weeks. Normally, the culture is carried out under 5% $CO_2$. The antibody titer of a supernatant of a hybridoma culture can be measured according to the same manner as that of the above-described measurement of anti-BSSP4 antibody titer in an antiserum. That is, examples of the measurement to be used include radioimmunoassay (RIA), enzyme-linked immunosorbent assay (ELISA), FIA (fluorescence immunoassay), plaque assay, agglutination reaction method, and the like. Among them, ELISA as shown blew is preferred.

Screening by ELISA

A protein prepared according to the same operation as that for an immunogen is immobilized on the surface of each well of an ELISA plate. Next, BSA, MSA, OVA, KLH, gelatin, skimmed milk, or the like is immobilized on each well to prevent non-specific adsorption. A supernatant of a hybridoma culture is added to each well and is allowed to stand for a given time so that an immunological reaction proceeds. Each well is washed with a washing solution such as PBS or the like. Preferably, a surfactant is added to this washing solution. An enzyme labeled secondary antibody is added and allowed to stand for a given time. As the enzyme to be used for the label, there can be used β-galactosidase, alkaline phosphatase, peroxidase and the like. After washing each well with the same washing solution, a substrate solution of the labeled enzyme used is added so that an enzymatic reaction proceeds. When the desired antibody is present in the supernatant of a hybridoma culture, the enzymatic reaction proceeds and the color of the substrate solution is changed.

Normally, cloning is carried out by a per se known method such as semi-solid agar method, limiting dilution method and the like. Specifically, after confirming a well in which the desired antibody is produced by the above-described method, cloning is carried out to obtain a single clone. For cloning, it is preferred to employ limiting dilution method wherein hybridoma cells are diluted so that one colony is formed per one well of a culture plate. For cloning by limiting dilution method, feeder cells can be used, or a cell growth factor such as interleukin 6, etc. can be added to improve colony forming capability. In addition, cloning can be carried out by using FACS and single cell manipulation method. The cloned hybridoma is preferably cultured in a serum-free culture medium and an optimal amount of an antibody is added to its supernatant. The single hybridoma thus obtained can be cultured in a large about by using a flask or a cell culture device, or cultured in the abdominal cavity of an animal (J. Immunol. Meth., 53, 313, 1982) to obtain a monoclonal antibody. When culturing in a flask, there can be used a cell culture medium (e.g., IMDM, DMEM, RPMI1640, etc.) containing 0 to 20% of FCS. When culturing in the abdominal cavity of an animal, the animal to be used is preferably the same species or the same line as that from which the myeloma cells used in the cell fusion are derived, a thymus deficient nude mouse or the like, and the hybridoma is transplanted after administration of a mineral oil such as pristane, etc. After 1 to 2 weeks, myeloma cells are proliferated in the abdominal cavity to obtain ascites containing a monoclonal antibody.

The monoclonal antibody of the present invention which does not cross-react with other proteins can be obtained by selecting a monoclonal antibody which recognizes an epitope specific to hBSSP4 or mBSSP4. In general, an epitope presented by an amino acid sequence composed of at least 3, preferably 7 to 20 successive amino acid residues in an amino acid sequence which constitutes a particular protein is said to be an inherent epitope of the protein. Then, a monoclonal antibody recognizing an epitope constituted by a peptide having an amino acid sequence composed of at least 3 successive amino acid residue selected from the amino acid residues disclosed in any of SEQ ID NOS: 2 and 4 can be said to be the monoclonal antibody specific for hBSSP4 or mBSSP4 of the present invention. An epitope common to BSSP4 family can be selected by selecting an amino acid sequence conservative among the amino acid sequences described in SEQ ID NOS: 2 and 4. Or, in case of a region containing an amino acid sequence specific for each sequence, a monoclonal antibody which can differentiate respective proteins can be selected.

Separation and purification of the anti-hBSSP4 or mBSSP4 monoclonal antibody, like a conventional polyclonal antibody, can be carried out according to the same manner as those of immunoglobulins. As a known purification method, there can be used a technique, for example, salting out, alcohol precipitation, isoelectric precipitation, electrophoresis, ammonium sulfate precipitation, absorption and desorption with an ion exchange material (e.g., DEAE), ultrafiltration, gel filtration, or specific purification by collecting only an antibody with an antibody-binding solid phase or an active adsorber such as protein A or protein G, etc., and dissociating the binding to obtain the antibody. For preventing formation of aggregates during purification or decrease in the antibody titer, for example, human serum albumin is added at a concentration of 0.05 to 2%. Alternatively, amino acids such as glycine, α-alanine, etc., in particular, basic amino acids such as lysine, arginine, histidine, etc., saccharides such as glucose, mannitol, etc., or salts such as sodium chloride, etc. can be added. In case of IgM antibody, since it is very liable to be aggregated, it may be treated with β-propionilactone and acetic anhydride.

The polyclonal antibody of the present invention can be produced according to a per se known method or its modification. For example, an immunogen (protein antigen) per se or a complex thereof with a carrier protein is prepared and, according to the same manner as that in the above monoclonal antibody production, a warm-blooded animal is immunized. A material containing an antibody against the protein of the present invention or its fragment is collected from the immunized animal and the antibody is separated and purified to obtain the desired antibody. As for a complex of an immunogen and a carrier protein for immunizing a warm-blooded animal, the kind of a carrier protein and the mixing ratio of a carrier and a hapten are not specifically limited in so far as an antibody against the hapten immunized by cross-linking with the carrier is efficiently produced. For example, there can be used about 0.1 to 20, preferably about 1 to 5 parts by weight of bovine serum albumin, bovine cycloglobulin, hemocyanin, etc. coupled with one part by weight of a hapten. For coupling a carrier and a hapten, various condensing agents can be used. Examples thereof include glutaraldehyde, carbodiimide or maleimide active ester, active ester agents having thiol group or dithiopyridyl group, and the like. The condensed product is administered as such or together with a carrier or diluent to a site of a warm-blooded animal where an antibody can be produced. For enhancing the antibody production, upon administration, Freund's complete adjuvant or Freund's incomplete adjuvant may be administrated. Normally, the administration is carried out once every 2 to 6 weeks, 3 to 10 times in all. The polyclonal antibody can be collected from blood, ascites, or the like, preferably blood of the immunized animal. The polyclonal antibody titer in an antiserum can be measured according to the same manner as measurement of the above monoclonal antibody titer in the antiserum. Separation and purification of the polyclonal antibody, like the above monoclonal antibody, can be carried out according to the same manner as those of immunoglobulins.

The monoclonal antibody and polyclonal antibody against hBSSP4 or mBSSP4 or a fragment thereof can be utilized for diagnosis and treatment of diseases associated with cells expressing hBSSP4 or mBSSP4. By using these antibodies, hBSSP4 or mBSSP4 or a fragment thereof can be determined based on their immunological binding to hBSSP4 or mBSSP4 or a fragment thereof of the present invention. Specifically, examples of a method for determining hBSSP4 or mBSSP4 or a fragment thereof in a specimen by using these antibodies include a sandwich method wherein the antibody attached to an insoluble carrier and the labeled antibody are reacted with hBSSP4 or mBSSP4 or a fragment thereof to form a sandwich complex and the sandwich complex is detected, as well as a competitive method wherein labeled hBSSP4 or mBSSP4, and hBSSP4 or mBSSP4 or a fragment thereof in the specimen are competitively reacted with the antibody and hBSSP4 or mBSSP4 or a fragment thereof in the specimen is determined based on the amount of the labeled antigen reacted with the antibody.

As a sandwich method for determining hBSSP4 or mBSSP4 or a fragment thereof, there can be used two step method, one step method and the like. In two step method, first, the immobilized antibody is reacted with hBSSP4 or mBSSP4 or a fragment thereof and then unreacted materials are completely removed by washing, followed by addition of the labeled antibody to form immobilized antibody-hBSSP4 or mBSSP4-labeled antibody. In one step method, the immobilized antibody, labeled antibody and hBSSP4 or mBSSP4 or a fragment thereof are added at the same time.

Examples of an insoluble carrier used for the determination include synthetic resins such as polystyrene, polyethylene, polypropylene, polyvinyl chloride, polyester, polyacrylate, nylon, polyacetal, fluorine plastic, etc.; polysaccharides such as cellulose, agarose, etc.; glass; metal; and the like. An insoluble carrier may be shaped in various forms, for example, tray, sphere, fiber, rod plate, container, cell, test tube, and the like. The antibody adsorbed by a carrier is stored at a cold place in the presence of an appropriate preservative such as sodium azide or the like.

For immobilization of the antibody, a known chemical bonding method or a physical adsorption can be used. Examples of a chemical bonding method include a method using glutaraldehyde; maleimide method using N-succusin-imidyl-4-(N-maleimidomethyl)cyclohexane-1-carboxylate, N-succusinimidyl-2-maleimide acetate or the like; carbodi-imide method using 1-ethyl-3-(3-dimethylaminopropyl)car-bodiimide hydrochloride; or the like. In addition, there are maleimidobenzoyl-N-hydroxysuccinimide ester method, N-succinimidyl-3-(2-pyridylthio)propionic acid method, bisdiazobenzidine method, and dipalmityllysine method. Or, it is possible to capture a complex formed beforehand by reacting a materiel to be tested with two antibodies, whose epitopes are different, with an immobilized a 3rd antibody against the antibody.

For labeling, it is preferred to use enzyme, fluorescent substance, luminous substance, radioactive substance, metal chelate, or the like. Examples of the enzyme include peroxidase, alkaline phosphatase, β-D-galactosidase, malate dehydrogenase, *Staphylococcus* nuclease, δ-5-steroidisomerase, α-glycerol phosphate dehydrogenase, triose phosphate isomerase, horseradish peroxidase, asparaginase, glucose oxidase, ribonuclease, urease, catalase, glucose-6-phosphate dehydrogenase, glucoamylase, acetylcholinesterase and the like. Examples of the fluorescent substance include fluorescein isothiocyanate, phycobiliprotein, rhodamine, phycoerythrin, phycocyanin, allophycocyanin, o-phthalaldehyde, and the like. Examples of the luminous substance include isoluminol, lucigenin, luminol, aromatic acridinium ester, imidazole, acrdinium salt and its modified ester, luciferin, luciferase, aequorin and the like. Examples of the radioactive substance include $^{125}I$, $^{127}I$, $^{131}I$, $^{14}C$, $^{3}H$, $^{32}P$, $^{35}S$ and the like. The labeling material is not limited to them and any material which can be used for immunological determination can be used. Further, a low molecular weight hapten such as biotin, dinitrophenyl, pyridoxal or fluorescamine may be attached to the antibody. Preferably, horseradish peroxidase is used as a labeling enzyme. This enzyme can be reacted with various substrates and can readily be attached to the antibody by periodate method.

When an enzyme is used as a labeling material, a substrate and, if necessary, a coloring enzyme is used for measuring its activity. In case of using peroxidase as the enzyme, $H_2O_2$ is used as a substrate and, as a coloring agent, there can be used 2,2'-azino-di-[3-ethylbenzthiazoline sulfonic acid] ammonium salt (ABTS), 5'-aminosalicylic acid, o-phenylenediamine, 4-aminoantipyrine, 3,3',5,5'-tetramethylbenzidine and the like. In case of using alkaline phosphatase as the enzyme, o-nitorphenylphosphate, p-nitrophenylphosphoric acid, or the like can be used as a substrate. In case of using β-D-galactosidase as the enzyme, fluorescein-d-(β-D-galactopyranoside), 4-methylumbelliphenyl-β-D-galactopyranoside, or the like can be used as a substrate. The present invention also include a kit comprising the above monoclonal antibody, polyclonal antibody and reagents.

As a cross-linking agent, a known cross-linking agent such as N,N'-o-phenylenedimaleimide, 4-(N-maleimidomethyl) cyclohexanoate-N-succinimide ester, 6-maleimidohexanoate-N-succineimide ester, 4,4'-dithiopyridine or the like can be utilized. The reaction of these cross-linking agents with enzymes and antibodies can be carried out by a known method according to properties of a particular cross-linking agent. Further, as the antibody, a fragment thereof, for example, Fab', Fab, F(b'2) can be used as the case may be. A labeled enzyme can be obtained by the same treatment regardless of whether the antibody is polyclonal or monoclonal. When the above labeled enzyme obtained by using a cross-linking agent is purified by a known method such as affinity chromatography or the like, a immunoassay system having more higher sensitivity can be obtained. The enzyme labeled and purified antibody is stored at a dark cold place with addition of a stabilizer such as thimerosal, glycerin or after lyophilization.

An objective to be determined is not specifically limited in so far as it is a sample containing BSSP4 or a fragment thereof, or a sample containing a precursor of BSSP4 or a fragment thereof and includes body fluids such as plasma, serum, blood, serum, urine, tissue fluid, cerebrospinal fluid and the like.

The following Examples further illustrate the present invention in detail but are not construed to limit the scope thereof.

EXAMPLE 1

Cloning of Novel Serine Protease mBSSP4 Gene

The cloning was carried out by PCR using a human brain cDNA library (Clontech) as a template and nucleotide sequences corresponding to an amino acid sequence common to serine proteases represented by

```
Primer 1:
GTG CTC ACN GCN GCB CAY TG      (SEQ ID NO:30)

Primer 2:
CCV CTR WSD CCN CCN GGC GA      (SEQ ID NO:31)
``` as primers. Namely, 5 μl of the template, 5 μl of 10× ExTaq buffer, 5 μl of DNTP, 10 pmol of each of the above primers and 0.5 μl of ExTaq (TAKARA) were added and the total volume was adjusted to 50 μl with sterilized water. PCR was carried out by repeating a cycle of heating at 94° C. for 0.5 minute, at 55° C. for 0.5 minute and then at 72° C. for 1 minutes, 35 times. The PCR product was mixed with pCR II-TOPO vector attached to TOPO TA cloning kit (Invitrogen) and the mixture was allowed to stand at room temperature for 5 minutes. Then, according to a conventional manner, *E. coli* Top 10 attached to the kit was transformed and applied to a LB (Amp⁺) plate (containing 100 μg/ml of ampicillin). According to a conventional manner, a plasmid was extracted from each colony obtained and its nucleotide sequence was determined by cycle sequencing method with a fluorescence sequencer (ABI). Homology of the sequence of each clone was examined by means of GenBank. Regarding an unknown sequence, i.e., BSSP4 gene, the full length cDNA was obtained by 5' RACE and 3' RACE and, according to the same manner as described above, the nucleotide sequence was determined. Namely, BSSP4 clone specific primers, GSP1 primers [hBSSP4F1 (SEQ ID NO: 32) or hBSSP4R1 (SEQ ID NO: 36)] and GSP2 primers [hBSSP4F2 (SEQ ID NO: 33) or hBSSP4R2 (SEQ ID NO: 37)] were prepared. PCR was carried out by using human brain Marathon-Ready cDNA (Clontech), AP1 primer attached to this reagent and either of the above GSP1 primers and heating at 94° C. for 2 minutes once and repeating a cycle of heating at 94° C. for 30 seconds, at 60° C. for 30 seconds and then at 72° C. for 30 seconds 35 times. Then, 5 μl of the PCR product diluted to 1/100, 5 μl of 10× buffer, 5 μl of dNTP, 10 pmol of either of 10 μM of the above GSP2 primer, 10 pmol of AP2 primer attached to the above reagent and 0.5 unit of ExTaq were admixed and adjusted to 50 μl with sterilized water. Then, according to the same manner as the above, PCR was carried out. The PCR product was cloned by the above TOPO TA cloning kit and sequenced to obtain the upstream and downstream regions of the above clone. At this time, as for a clone which seemed not to cover the full length of a protein, the specific primers shown hereinafter were prepared based on the newly found nucleotide sequence. Further, based on this sequence, the primers capable of amplifying ORF as shown hereinafter [hBSSP4F6 (SEQ ID NO: 35) and hBSSP4R3/E (SEQ ID NO: 38) or hBSSP4R4/E (SEQ ID NO: 39)] were prepared and PCR carried out using human brain Marathon-ready cDNA as a template to confirm that these clones were identical. This was cloned into pCR II-TOPO vector attached to TOPO TA cloning kit to obtain the plasmid pCR II/hBSSP4 containing the full length cDNA clone. The nucleotide sequence of DNA contained in this plasmid is shown in SEQ ID NO: 1 and the amino acid sequence of hBSSP4 protein deduced from the nucleotide sequence is shown in SEQ ID NO: 2. Further, two different types of clones were obtained. The amino acid sequence of hBSSP4 represented by SEQ ID NO: 2 (the 1st to 268th amino acids) is hBSSP4 mature or active type protein composed of 268 amino acids. In the amino acid sequence represented by SEQ ID NO: 2, the -49th to -1st amino acids are a prepro or pro part and the -15th to -1st amino acids are a pro part and are considered to be a precursor of hBSSP4. As consensus sequences of serine proteases, there are Ala-Ala-His-Cys represented by the 39th to 42nd amino acid residues of SEQ ID NO:2 and Asp-Ser-Gly-Gly-Pro represented by the 192nd to 196th amino acid residues of SEQ ID NO:2 and there are one or more Asp's between these consensus sequences.

Further, 8 clones having different nucleotide sequences, perhaps, caused by alternative splicing were obtained. The nucleotide sequences thereof are shown in SEQ ID NOS: 3, 5, 7, 9, 11, 13, 15 and 17. Further, the amino acid sequences thereof deduced from these nucleotide sequences are shown in SEQ ID NOS: 4, 6, 8, 10, 12, 14, 16 and 18. As described above, in these sequences, there are those having either or bot consensus sequences of serine proteases and those having no consensus sequences of serine proteases. There is a possibility that these gene products (transcription product or translation product) have a function of control factors for serine proteases.

According to the same manner, 5' RACE and 3' RACE were carried out by using the primers as described hereinafter and mouse brain Marathon-Ready cDNA (Clontech) as a template, followed by cloning to obtain mouse homologous gene pCRII/mBSSP4. The nucleotide of DNA containing this plasmid is shown by SEQ ID NO:19 and the amino acid sequence of mBSSP4 protein deduced from this nucleotide sequence is shown in SEQ ID NO:20. The amino acid sequence of mBSSP4 represented by SEQ ID NO:20 (the 1st to 259th amino acids) is mBSSP4 mature or active type protein composed of 259 amino acids. In the amino acid sequence represented by SEQ ID NO:20, the -49th to 1st amino acids are a prepro or pro part and the -15th to -1st amino acids are a pro part and are considered to be a precursor of mBSSP4. As consensus sequences of serine proteases, there are Ala-Ala-His-Cys (the 39th to 42nd amino acid residues of SEQ ID NO:20) and Asp-Ser-Gly-Gly-Pro (the 192nd to 196th amino acid residues of SEQ ID NO:20) and there are one or more Asp's between the consensus sequences.

```
human BSSP4
hBSSP4F1    Forward  AGGTTCCTATCATCGACTCG              RACE    (SEQ ID NO:32)

hBSSP4F2    Forward  TGAGGACATGCTGTGTGCCGG             RACE    (SEQ ID NO:33)

hBSSP4F3    Forward  GTTGTGGGCGGCGAGGACAG              mature  (SEQ ID NO:34)

hBSSP4F6    Forward  GCCATGGTGGTTTCTGGAGC              FL*     (SEQ ID NO:35)

hBSSP4R1    Reverse  TATGGTTTGTTCAGGTTGTCC             RACE    (SEQ ID NO:36)

hBSSP4R2    Reverse  AGGGCAATGTCTGCACAGGC              RACE    (SEQ ID NO:37)

hBSSP4R3/E  Reverse  CTGAATTCCTAGGAGCGCGCGGCGGCC       FL*     (SEQ ID NO:38)

hBSSP4R4/E  Reverse  GAGAATTCGATATGTGGGCAGGGTTACA      FL*     (SEQ ID NO:39)

mouse BSSR4
mBSSP4.1    Forward  ACAAACCATCTCTGTTCTCAG             RACE    (SEQ ID NO:40)

mBSSP4F2    Forward  GTCCCAGAAAGTAGGCATTG              RACE    (SEQ ID NO:41)

mBSSP4F3    Forward  CTCCACCCATACCAGCAATG              FL*     (SEQ ID NO:42)

mBSSP4F4    Forward  ATTGTGGGAGGTGAGGACAG              mature  (SEQ ID NO:43)

mBSSP4.2    Reverse  TGCAGAGTTCGGAGTCGATG              RACE    (SEQ ID NO:44)

mBSSP4R2    Reverse  ATCCAGCAGTCGGTCTTGGG              RACE    (SEQ ID NO:45)

mBSSP4R3/P  Reverse  ATTCTGCAGTTCCTTGTTCTCTCGCTCAGG   FL*     (SEQ ID NO:46)
*for full length
```

EXAMPLE 2

Expression hBSSP4 or mBSSP4 Gene in Human being and

Figure 4:
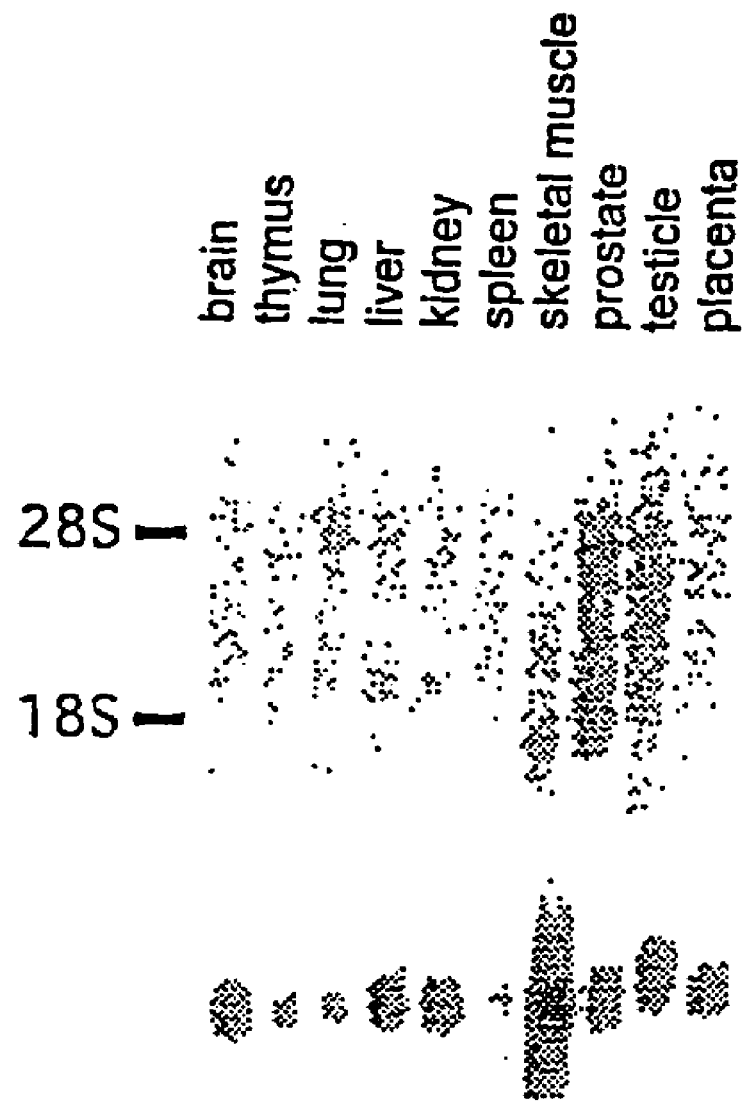
FIG. 4 illustrates the results of northern blotting using mRNA prepared in Example 2 hereinafter.
Figure 5:
FIG. 5 illustrates the results of northern blotting using mRNA prepared in Example 2 hereinafter.

Mouse Internal Organs According to the protocol of QuickPrep Micro mRNA purification Kit (Amersham-Pharmacia), mRNAs were isolated from various internal organs of Balb/c mice or their fetuses. They were subjected to electrophoresis according to a conventional manner and transcribed to a nylon membrane. A probe was prepared separately by isolating a part of a nucleotide sequence encoding the mature protein of mBSSP4 from pCR II/mBSSP4, purifying it and labeling it with $\alpha$-$^{32}$P dCTP. The probe was diluted with 5×SSC and reacted with the above membrane filter at 65° C. for a whole day and night. Likewise, a probe was prepared by isolating a part of a nucleotide sequence encoding the mature protein of hBSSP4 from pCR II/hBSSP4, purifying it and labeling it with $\alpha$-$^{32}$P dCTP, and diluted with 5×SSC and the dilution was reacted with human multiple tissue blot, human multiple tissue blot II and human brain multiple blot II (Clontech) membrane. Then, the filter was washed twice each with 2×SSC/0.1% SDS at room temperature for 30 minutes, 1×SSC/0.1% SDS at room temperature for 30 minutes and 0.1×SSC/0.1% SDS at 65° C. for 30 minutes. The filter was exposed to an imaging plate for FLA2000 (Fuji Film) for one day to analyze the expression. The results shown in the drawings are those obtained by using human multiple tissue blot membrane (FIG. 1), human multiple tissue blot II membrane (FIG. 2), human brain multiple blot II membrane (FIG. 3) and mRNAs prepared from various internal organs of 3-month-old mice (FIG. 4) and mRNAs prepared from prostates of 1-month-old, 3-month-old and 12-month-old mice (FIG. 5). In addition, the mRNAs prepared above were subjected to RT-PCR by using Ready To Go RT-PCR Beads (Amersham-Pharmacia) and hBSSP4 and mBSSP4 gene specific primers (human being: SEQ ID NOS: 33 and 38 or 39, mouse: SEQ ID NOS: 40 and 44) according to the protocol attached to the kit.

Figure 2:
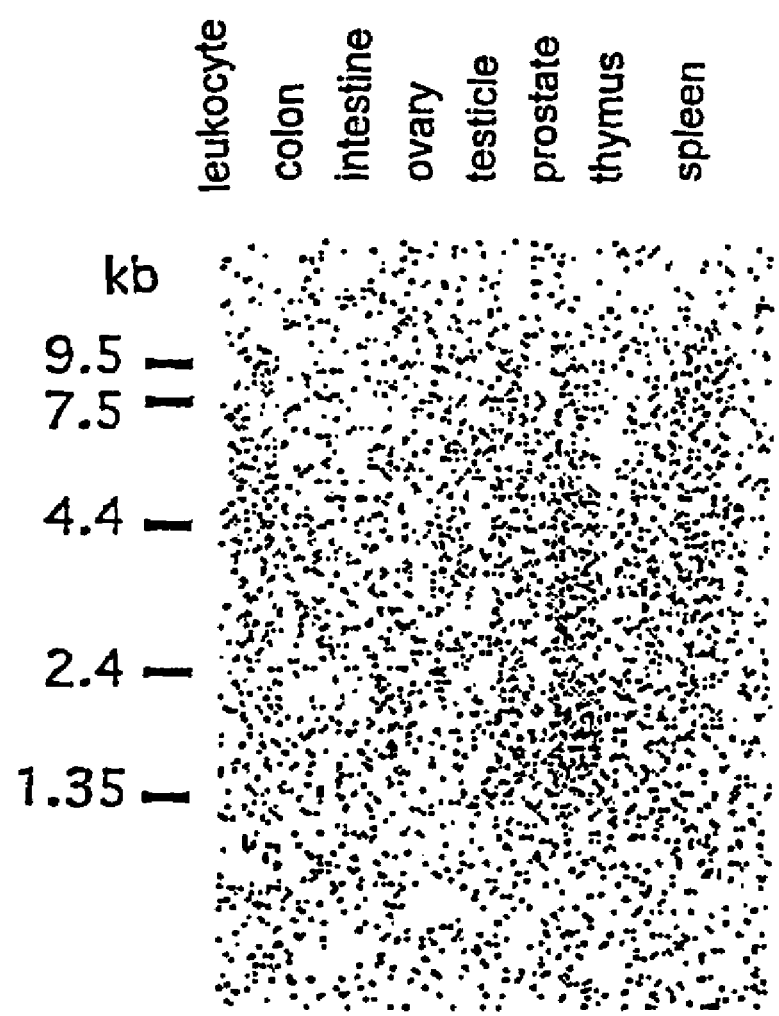
FIG. 2 illustrates the results of northern blotting using human multiple tissue blot II membrane.
Figure 3:
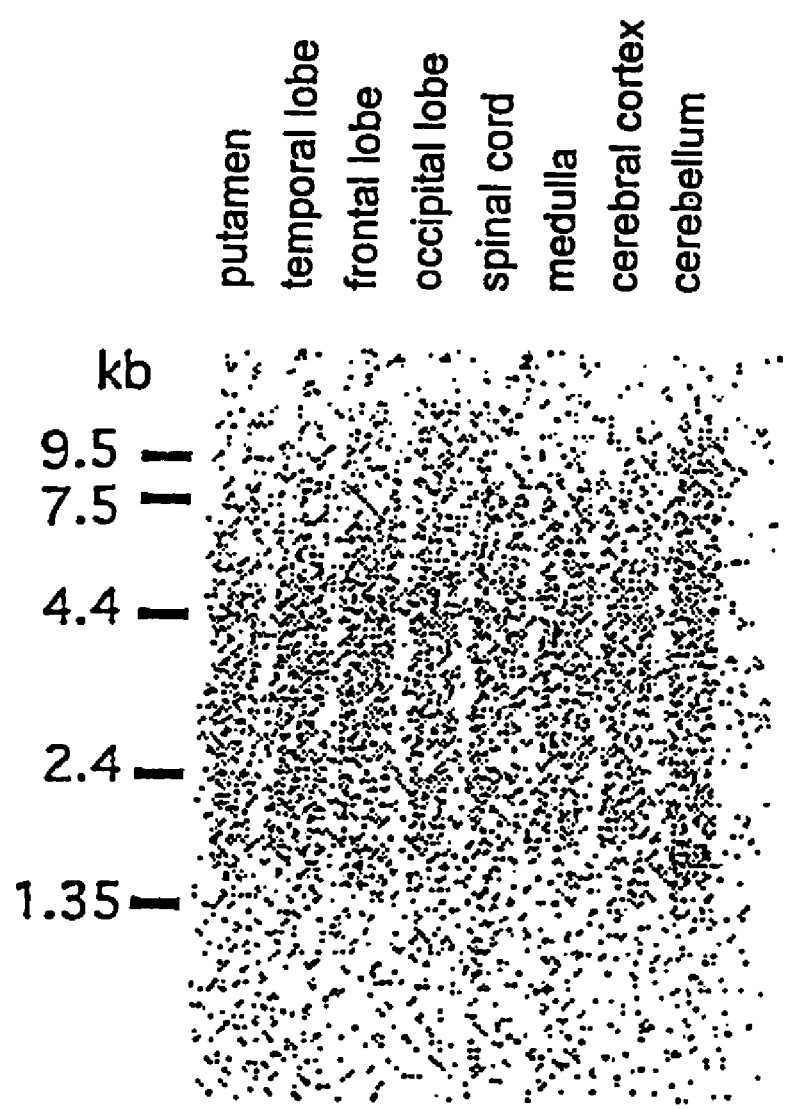
FIG. 3 illustrates the results of northern blotting using human multiple tissue blot II membrane.

As seen form FIGS. 1 to 3, in case of northern blotting analysis, the expression of hBSSP4 was recognized in prostate (FIG. 2, the band between 1.35 to 2.4 kb) and cerebllum (FIG. 3, the band between 1.35 and 2.4 kb). The expression of mBSSP4 was recognized in prostate and skeletal muscle (FIG. 4). Further, according to the results of RT-PCR, the expression of hBSSP4 was recognized in brain, placenta, testicle and prostate of from fetuses to adults of human beings and the expression of mBSSP4 was recognized in prostate of newborns to adults of mice. Then, it is considered that the novle serine proteases of the present invention have various roles in brain, prostate, placenta, testicle and skeletal muscle. Further, the presence of the transcribed product (about 1.4 to 1.5 kb) having the nucleotide sequence of SEQ ID NO: 7 has been confirmed by the above northern blotting analysis.

EXAMPLE 3

Expression of Novel Serine Proteases Encoded by hBSSP4 or mBSSP4 Gene (1) Construction of Expression Plasmid A cDNA region encoding the mature form of hBSSP4 or mBSSP4 protein was amplified by PCR using the plasmid pCR II/hBSSP4 or pCR II/mBSSP4 as a template (the primers used were those having the sequences of SEQ ID NOS: 34 and 39 for a human being and those having the sequences of SEQ ID NOS: 43 and 46 for mouse). The PCR product was ligated to pTrc-HisB (Invitrogen) which had been digested with BamHI and blunted with mung bean nuclease. E. coli JM109 was transformed by the resultant and colonies formed were analyzed by PCR to obtain E. coli containing the desired serine protease expressing plasmid pTrcHis/hBSSP4 or pTrcHis/mBSSP4.

The resultant E. coli strains were designated E. coli pTrcHis/hBSSP4 and E. coli pTrcHis/mBSSP4, respectively, and deposited at National Institute of Bioscience and Human-Technology (NIBH), Agency of Industrial Science & Technology of 1-1-3 Higashi, Tsukuba-shi, Ibaraki-ken, Japan on Oct. 29, 1998 under the accession numbers of FERM P-17037 and FERM P-17034, respectively.

(2) Expression of Protein by E. coli Containing Expression Plasmid

A single colony of E. coli having the expression plasmid was inoculated in 10 ml of LB (Amp$^+$) culture medium and incubated at 37° C. overnight. This was inoculated in 250 ml of LB (Amp$^+$) culture medium and incubated at 37° C. When the absorbance at 600 nm became 0.5, 250 µl of 0.1 M IPTG (isopropyl-β-D-(-)-thiogalactopyranoside) was added and the incubation was continued for additional 5 hours. The E. coli was centrifuged and suspended in a cell disruption buffer (10 mM phosphate buffer pH 7.5, 1 mM EDTA) and sonicated on ice to disrupt E. coli. This was centrifuged at 14,000 r.p.m. for 20 minutes to obtain a precipitate. The precipitate was washed twice with a cell disruption buffer containing 0.5% Triton X-100™ and washed with water to remove Triton X-100™. Then, the resultant mixture was dissolved by soaking in a denaturation buffer containing 8 M urea (8M urea, 50 mM Tris pH8.5, 20 mM ME) at 37° C. for 1 hour. The solution was passed through TALON metal affinity resin (Clontech), washed with the denaturation buffer containing 10 mM imidazole, and then eluted with the denaturation buffer containing 100 mM imidazole to purify the solution. The purified product was dialyzed against PBS for 3 days with exchanging the buffer every other night to obtain the protein hBSSP4-His or mBSSP4-His.

EXAMPLE 4

Expression of Novel Serine Protease Mature Protein Encoded by hBSSP4 Gene by Using pFBTrypSigTag/hBSSP4

(1) Construction of pFBTrypSigTag/hBSSP4

The sequences represented by SEQ ID NOS: 21 and 22 were subjected to annealing and digested with NheI and BamHI. The resultant fragment was inserted into Nhe-1-BamHI digested pSecTag2A (Invitrogen) to obtain pSecTrypHis. Twenty units of BamHI was added to 5 µg of pSecTrypHis vector and the vector was cleaved at 37° C. over 4 hours. Then, 6 units of mung bean nuclease (TAKARA) was added thereto and reacted at room temperature (25° C.) for 30 minutes to blunt the terminal ends. Further, the 3'-terminus side of the cloning site was cleaved with 20 units of XhoI, 1 unit of bacterial alkaline phosphatase (TAKARA) was added thereto and the reaction was carried out at 65° C. for 30 minutes.

Figure 6:
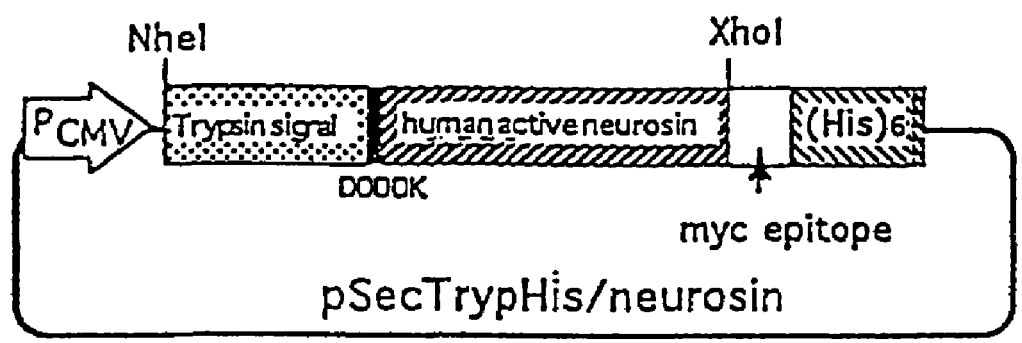
FIG. 6 illustrates the plasmid constructed by the method of Example 4 hereinafter.

According to the same manner as that described in JP 9-149790 A or Biochim. Biophys. Acta, 1350, 11, 1997, mRNA was prepared from COLO201 cells and cDNA was synthesized to obtain the plasmid pSPORT/neurosin. cDNA of an active region of neurosin was obtained from pSPORT/neurosin by PCR using primers having the sequences represented by SEQ ID NOS: 23 and 24. Ten units of XhoI was reacted with the PCR product at 37° C. for 3 hours to cleave XhoI site at the 3'-side thereof. This was inserted into pSecTrypHis by TAKARA ligation kit to obtain pSecTrypHis/neursoin (FIG. 6).

Amplification was carried out by using the primers having the sequences represented by SEQ ID NOS: 25 and 26 so that the peptide of Leu-Val-His-Gly SEQ ID NO:52 was present at the C-terminus of the part from trypsin signal to the enterokinase recognition site of pSecTrypHis/neurosin. This was inserted between NheI and HindIII sites of pSecTag2A to construct the plasmid pTrypSig.

One μg (0.1 μl) of the plasmid pSecTab2A was treated with the restriction enzymes NheI and BamHI to completely remove a region encoding the leader sequence of IgGk. One hundred pmol portions of DANs represented by SEQ ID NOS: 47 and 48 were added to the resultant solution and the mixture was heated at 70° C. for 10 minutes and subjected to annealing by allowing to stand at room temperature for 30 minutes. Two μl of I solution of DNA ligation kit Ver. 2 (TAKARA) was added to 1 μl portions of His secretory signal sequence and pSecTag2A treated by NheI and BamHI and the reaction was carried out at 16° C. for 30 minutes.

To the reaction mixture was add 0.1 ml of E. coli competent cell XL1-Blue (STRATAGENE) and reacted on ice for 30 minutes. Then, the reaction mixture was subjected to heat shock at 42° C. for 60 seconds. After standing on ice for 2 minutes, 0.9 ml of SOC culture medium (Toyo Boseki K.K.) was added thereto and the mixture was shaken with a shaker at 37° C. for 1 hour. The mixture was centrifuged at 5,000 r.p.m. for 1 minutes and the supernatant was discarded. The precipitated competent cells were suspended in the liquid remained in the centrifuge tube and the suspension was applied to an ampicillin LB plates containing 100 μg/ml of ampicillin. The plates were incubated at 37° C. overnight. Among the colonies formed, a colony into which DNA of His secretory signal was inserted was selected by PCR to obtain pTrypHis.

Figure 7:
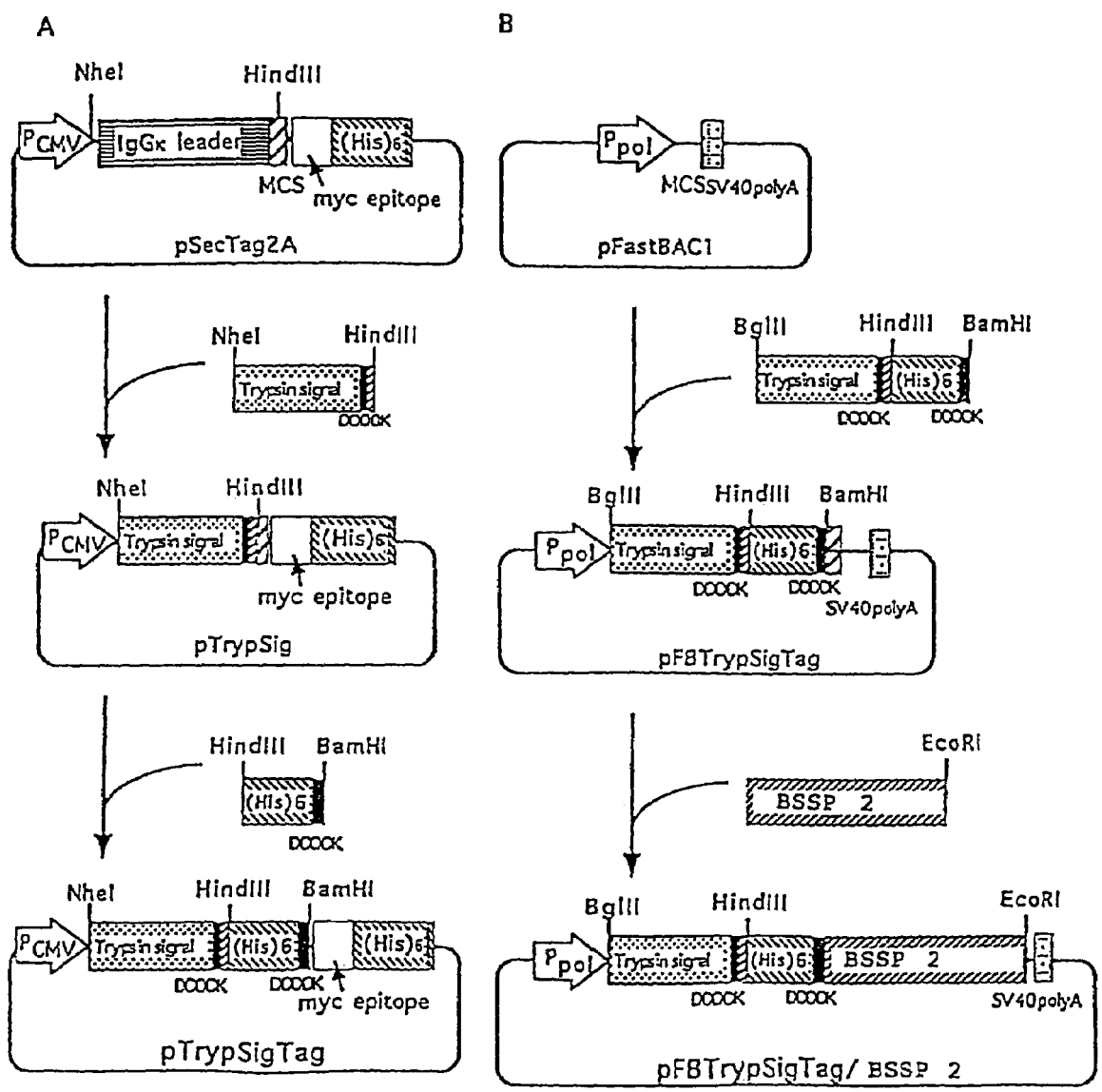
FIG. 7 illustrates the construction of the plasmid by the method of Example 4 hereinafter.

A sequence of about 200 bp containing His Tag region of pTrypHis was amplified by using primers having the sequence represented by SEQ ID NOS: 26 and 27 and a fragment of about 40 bp containing His Tag and enterokinase recognizing site formed by digestion of HindIII and BamHI was inserted into pTrypSig to construct pTrypSigTag (FIG. 7A).

cDNA was prepared by PCR of the sequence from trypsin signal to enterokinase recognizing site of pTrypSigTag using primers having the sequences represented by SEQ ID NOS: 24 and 28 and cut out by digestion with BglII and BamHI. It was inserted into BamHI site of pFastBAC1 (GIBCO). The insertion direction was confirmed by PCR using primers having the sequences represented by SEQ ID NOS 24 and 29. A clone into which the cDNA was inserted in the direction toward transcription and translation by polyhedrin promoter was selected to obtain pFBTrypSigTag.

Twenty units of BamHI was added to 5 μg of pFBTrypSigTag vector and the vector was cleaved at 37° C. over 4 hours, followed by addition of 6 units of mung bean nuclease (TAKARA) and reaction at room temperature (25° C.) for 30 minutes to blunt the terminal ends. Further, the 3'-side of the cloning site was cleaved by 20 units of EcoRI, followed by addition of 1 unit of bacterial alkaline phosphatase (TAKARA). The reaction was carried out at 65° C. for 30 minutes.

cDNA of the active region of hBSSP4 was obtained by PCR according to a conventional manner using pTrcHis/hBSSP4 prepared from E. coli pTrcHis/hBSSP4 (accession No. FERM P-17037) or pCRII/hBSSP4. The resultant cDNA was inserted into pFBTrypSigTag to obtain pFBTrypSigTag/hBSSP4 (FIG. 7B). At this time, correct insertion of hBSSP4 was confirmed by determining the sequence.

Bacmid DNA was transformed with pFBTrypSigTag/hBSSP4 according to a protocol of Gibco BRL BAC-TO-BAC baculovirus expression system to prepare a recombinant bacmid having chimera hBSSP4 fused with trypsinogen signal peptide, His tag and enterokinase recognizing site. When this was expressed in Sf-9 cell according to a manual of BAC-TO-BAC baculovirus expression system, it was secreted in the culture supernatant from 2 days after infection of the virus.

According to the same manner as described above, pFETrypSigTag/mBSSP4 can be prepared and secreted by using pTrcHis/mBSSP4 obtained from E. coli pTricHis/mBSSP4 (accession No. FERM P-17034) or pCRII/mBSSP4 obtained in Example 1.

(2) Determination of Enzyme Activity

The recombinant fused protein hBSSP4 obtained in the culture supernatant was passed through a chelate column to purify it and, after dialysis, its enzyme activity was determined. First, the culture supernatant was applied to a chelate column (Ni-NTA-Agarose, Qiagen) with PBS buffer and eluted stepwise with a solution of imidazole (Wako Pure Chemical Industries, Ltd.) dissolved in PBS. The resultant imidazole-eluted fraction was applied to a PD-10 column (Pharmacia) to exchange to PBS buffer. Fifty μl of this sample was mixed with 10 μl of enterokinase (1 U/1 μl, Invitrogen) and the reaction was carried out at room temperature for 60 minutes. Each of various synthetic substrates (Peptide Laboratory, Boc-Gln-Ala-Arg-MCA, Boc-Phe-Ser-Arg-MCA, Bz-Arg-MCA, Boc-Val-Leu-Lys-MCA, Pyr-Gly-Arg-MCA, Pro-Phe-Arg-MCA, Boc-Val-Pro-Arg-MCA, Z-Arg-Arg-MCA, Arg-MCA, Z-Phe-Arg-MCA) was dissolved in DMSO and diluted with 1 M Tris-HCl (pH 8.0) to obtain a substrate solution. Fifty μl of 0.2 M substrate solution was added thereto and further the reaction was carried out at 37° C. After one hour, the fluorescence of AMC (7-amino-4-methylcoumalin) formed by the enzymatic reaction was measured at 380 nm of excitation wavelength and 460 nm of fluorescence wavelength to determine the activity.

As a result, the recombinant fused protein hBSSP4 has been shown to have serine protease activity. Likewise, mBSSP4 derived from a mouse showed the activity.

INDUSTRIAL UTILITY

According to the present invention, there are provided isolated human and mouse serine protease (hBSSP4 and mBSSP4) polynucleotides, their homologous forms, mature forms, precursors and polymorphic variants. Further, according to the present invention, there are provided hBSSP4 and mBSSP4 proteins as well as compositions containing hBSSP4 and mBSSP4 polynucleotides and proteins, their production and use.

Sequence Listing Free Text

SEQ ID NO: 21: Designed oligonucleotide to construct plasmid pSecTrypHis

SEQ ID NO: 22: Designed oligonucleotide to construct plasmid pSecTrypHis

SEQ ID NO: 23: Designed oligonucleotide primer to amplify neurosin-encoding sequence SEQ ID NO: 24: Designed oligonucleotide primer to amplify neurosin-encoding sequence SEQ ID NO: 25: Designed oligonucleotide primer to amplify a portion of plasmid pSecTrypHis/Neurosin SEQ ID NO: 26: Designed oligonucleotide primer to amplify a portion of plasmid pSecTrypHis/Neurosin SEQ ID NO: 27: Designed oligonucleotide primer to amplify a portion of plasmid pTrypHis SEQ ID NO: 28: Designed oligonucleotide primer to amplify a portion of plasmid pTrypSigTag SEQ ID NO: 29: Designed oligonucleotide primer to amplify a portion of plasmid pFBTrypSigTag SEQ ID NO: 30: Designed oligonucleotide primer to amplify conserved region of serin proteases-encoding sequence; n is a, c, g or t.

SEQ ID NO: 31: Designed oligonucleotide primer to amplify conserved region of serin proteases-encoding sequence; n is a, c, g or t.

SEQ ID NO: 32: Designed oligonucleotide primer designated as hBSSP4F1 for RACE for human BSSP4 (forward)

SEQ ID NO: 33: Designed oligonucleotide primer designated as hBSSP4F2 for RACE for human BSSP4 (forward)

SEQ ID NO: 34: Designed oligonucleotide primer designated as hBSSP4F3 to amplify mature human BSSP4-encoding region (forward)

SEQ ID NO: 35: Designed oligonucleotide primer designated as hBSSP4F6 to amplify full-length human BSSP4-encoding mRNA (forward)

SEQ ID NO: 36: Designed oligonucleotide primer designated as hBSSP4R1 for RACE for human BSSP4 (reverse)

SEQ ID NO: 37: Designed oligonucleotide primer designated as hBSSP4R2 for RACE for human BSSP4 (reverse)

SEQ ID NO: 38: Designed oligonucleotide primer designated as hBSSP4R3/E to amplify full-length human BSSP4-encoding mRNA (reverse)

SEQ ID NO: 39: Designed oligonucleotide primer designated as hBSSP4R4/E to amplify full-length human BSSP4-encoding mRNA (reverse)

SEQ ID NO: 40: Designed oligonucleotide primer designated as mBSSP4.1 for RACE for mouse BSSP4 (forward)

SEQ ID NO: 41: Designed oligonucleotide primer designated as mBSSP4F2 for RACE for mouse BSSP4 (forward)

SEQ ID NO: 42: Designed oligonucleotide primer designated as mBSSP4F3 to amplify full-length mouse BSSP4-encoding mRNA (forward)

SEQ ID NO: 43: Designed oligonucleotide primer designated as mBSSP4F4 to amplify mature mouse BSSP4-encoding region (forward)

SEQ ID NO: 44: Designed oligonucleotide primer designated as mBSSP4.2 for RACE for mouse BSSP4 (reverse)

SEQ ID NO: 45: Designed oligonucleotide primer designated as mBSSP4R2 for RACE for mouse BSSP4 (reverse)

SEQ ID NO: 46: Designed oligonucleotide primer designated as mBSSP4R3/P to amplify full-length mouse BSSP4-encoding mRNA (reverse)

SEQ ID NO: 47: Designed oligonucleotide to construct plasmid pTrypHis

SEQ ID NO: 48: Designed oligonucleotide to construct plasmid pTrypHis

What is claimed is:

1. An isolated protein selected from the group consisting of:
  (a) a protein having the amino acid sequence composed of 270 amino acids represented by the $1^{st}$ to $270^{th}$ amino acids of SEQ ID NO:4;
  (b) a protein having the amino acid sequence composed of 319 amino acids represented by the $-49^{th}$ to $270^{th}$ amino acids of SEQ ID NO:4; and
  (c) a protein having the amino acid sequence composed of 285 amino acids represented by the $-15^{th}$ to $270^{th}$ amino acids of SEQ ID NO:4.

2. A composition, comprising the isolated protein according to claim 1.

* * * * *

SEQUENCE LISTING

```
<160> NUMBER OF SEQ ID NOS: 52

<210> SEQ ID NO 1
<211> LENGTH: 1282
<212> TYPE: DNA
<213> ORGANISM: Homo sapiens
<220> FEATURE:
<221> NAME/KEY: CDS
<222> LOCATION: (4)..(954)
<223> OTHER INFORMATION:
<220> FEATURE:
<221> NAME/KEY: mat_peptide
<222> LOCATION: (151)..()
<223> OTHER INFORMATION:

<400> SEQUENCE: 1 gcc atg gtg gtt tct gga gcg ccc cca gcc ctg ggt ggg ggc tgt ctc        48
    Met Val Val Ser Gly Ala Pro Pro Ala Leu Gly Gly Gly Cys Leu
            -45                 -40                 -35 ggc acc ttc acc tcc ctg ctg ctg ctg gcg tcg aca gcc atc ctc aat        96
Gly Thr Phe Thr Ser Leu Leu Leu Leu Ala Ser Thr Ala Ile Leu Asn
        -30                 -25                 -20 gcg gcc agg ata cct gtt ccc cca gcc tgt ggg aag ccc cag cag ctg       144
Ala Ala Arg Ile Pro Val Pro Pro Ala Cys Gly Lys Pro Gln Gln Leu
            -15                 -10                 -5 aac cgg gtt gtg ggc ggc gag gac agc act gac agc gag tgg ccc tgg       192
Asn Arg Val Val Gly Gly Glu Asp Ser Thr Asp Ser Glu Trp Pro Trp
     -1  1                   5                  10 atc gtg agc atc cag aag aat ggg acc cac cac tgc gca ggt tct ctg       240
Ile Val Ser Ile Gln Lys Asn Gly Thr His His Cys Ala Gly Ser Leu
15                  20                  25                  30
```

| | | |
|---|---|---|
| ctc acc agc cgc tgg gtg atc act gct gcc cac tgt ttc aag gac aac<br>Leu Thr Ser Arg Trp Val Ile Thr Ala Ala His Cys Phe Lys Asp Asn<br>                          35                       40                     45 | 288 |
| ctg aac aaa cca tac ctg ttc tct gtg ctg ctg ggg gcc tgg cag ctg<br>Leu Asn Lys Pro Tyr Leu Phe Ser Val Leu Leu Gly Ala Trp Gln Leu<br>            50                     55                     60 | 336 |
| ggg aac cct ggc tct cgg tcc cag aag gtg ggt gtt gcc tgg gtg gag<br>Gly Asn Pro Gly Ser Arg Ser Gln Lys Val Gly Val Ala Trp Val Glu<br>   65                     70                     75 | 384 |
| ccc cac cct gtg tat tcc tgg aag gaa ggt gcc tgt gca gac att gcc<br>Pro His Pro Val Tyr Ser Trp Lys Glu Gly Ala Cys Ala Asp Ile Ala<br>        80                     85                     90 | 432 |
| ctg gtg cgt ctc gag cgc tcc ata cag ttc tca gag cgg gtc ctg ccc<br>Leu Val Arg Leu Glu Arg Ser Ile Gln Phe Ser Glu Arg Val Leu Pro<br>95                   100                   105                 110 | 480 |
| atc tgc cta cct gat gcc tct atc cac ctc cct cca aac acc cac tgc<br>Ile Cys Leu Pro Asp Ala Ser Ile His Leu Pro Pro Asn Thr His Cys<br>               115                   120                 125 | 528 |
| tgg atc tca ggc tgg ggg agc atc caa gat gga gtt ccc ttg ccc cac<br>Trp Ile Ser Gly Trp Gly Ser Ile Gln Asp Gly Val Pro Leu Pro His<br>         130                   135                 140 | 576 |
| cct cag acc ctg cag aag ctg aag gtt cct atc atc gac tcg gaa gtc<br>Pro Gln Thr Leu Gln Lys Leu Lys Val Pro Ile Ile Asp Ser Glu Val<br>   145                   150                 155 | 624 |
| tgc agc cat ctg tac tgg cgg gga gca gga cag gga ccc atc act gag<br>Cys Ser His Leu Tyr Trp Arg Gly Ala Gly Gln Gly Pro Ile Thr Glu<br>160                  165                   170 | 672 |
| gac atg ctg tgt gcc ggc tac ttg gag ggg gag cgg gat gct tgt ctg<br>Asp Met Leu Cys Ala Gly Tyr Leu Glu Gly Glu Arg Asp Ala Cys Leu<br>175                  180                   185                 190 | 720 |
| ggc gac tcc ggg ggc ccc ctc atg tgc cag gtg gac ggc gcc tgg ctg<br>Gly Asp Ser Gly Gly Pro Leu Met Cys Gln Val Asp Gly Ala Trp Leu<br>         195                   200                 205 | 768 |
| ctg gcc ggc atc atc agc tgg ggc gag ggc tgt gcc gag cgc aac agg<br>Leu Ala Gly Ile Ile Ser Trp Gly Glu Gly Cys Ala Glu Arg Asn Arg<br>              210                   215                 220 | 816 |
| ccc ggg gtc tac atc agc ctc tct gcg cac cgc tcc tgg gtg gag aag<br>Pro Gly Val Tyr Ile Ser Leu Ser Ala His Arg Ser Trp Val Glu Lys<br>   225                   230                 235 | 864 |
| atc gtg caa ggg gtg cag ctc cgc ggg cgc gct cag ggg ggt ggg gcc<br>Ile Val Gln Gly Val Gln Leu Arg Gly Arg Ala Gln Gly Gly Gly Ala<br>240                  245                   250 | 912 |
| ctc agg gca ccg agc cag ggc tct ggg gcc gcc gcg cgc tcc<br>Leu Arg Ala Pro Ser Gln Gly Ser Gly Ala Ala Ala Arg Ser<br>255                  260                   265 | 954 |
| tagggcgcag cgggacgcgg ggctcggatc tgaaaggcgg ccagatccac atctggatct | 1014 |
| ggatctgcgg cggcctcggg cggtttcccc cgccgtaaat aggctcatct acctctacct | 1074 |
| ctgggggccc ggacggctgc tgcggaaagg aaaccccctc cccgacccgc cgacggcct | 1134 |
| caggccccgc cctccaaggc atcaggcccc gcccaacggc ctcatgtccc cgcccccacg | 1194 |
| acttccggcc ccgcccccgg ccccagcgc ttttgtgtat ataaatgtta atgattttta | 1254 |
| taggtatttg taaccctgcc cacatatc | 1282 |

<210> SEQ ID NO 2
<211> LENGTH: 317
<212> TYPE: PRT
<213> ORGANISM: Homo sapiens

<400> SEQUENCE: 2

```
Met Val Val Ser Gly Ala Pro Pro Ala Leu Gly Gly Gly Cys Leu Gly
            -45                 -40                     -35

Thr Phe Thr Ser Leu Leu Leu Ala Ser Thr Ala Ile Leu Asn Ala
            -30             -25             -20

Ala Arg Ile Pro Val Pro Ala Cys Gly Lys Pro Gln Gln Leu Asn
        -15             -10              -5

Arg Val Val Gly Gly Glu Asp Ser Thr Asp Ser Glu Trp Pro Trp Ile
 -1  1               5                  10                  15

Val Ser Ile Gln Lys Asn Gly Thr His His Cys Ala Gly Ser Leu Leu
                 20                  25                  30

Thr Ser Arg Trp Val Ile Thr Ala Ala His Cys Phe Lys Asp Asn Leu
            35                  40                  45

Asn Lys Pro Tyr Leu Phe Ser Val Leu Leu Gly Ala Trp Gln Leu Gly
        50                  55                  60

Asn Pro Gly Ser Arg Ser Gln Lys Val Gly Val Ala Trp Val Glu Pro
        65                  70                  75

His Pro Val Tyr Ser Trp Lys Glu Gly Ala Cys Ala Asp Ile Ala Leu
 80                  85                  90                  95

Val Arg Leu Glu Arg Ser Ile Gln Phe Ser Glu Arg Val Leu Pro Ile
                100                 105                 110

Cys Leu Pro Asp Ala Ser Ile His Leu Pro Pro Asn Thr His Cys Trp
            115                 120                 125

Ile Ser Gly Trp Gly Ser Ile Gln Asp Gly Val Pro Leu Pro His Pro
            130                 135                 140

Gln Thr Leu Gln Lys Leu Lys Val Pro Ile Ile Asp Ser Glu Val Cys
            145                 150                 155

Ser His Leu Tyr Trp Arg Gly Ala Gly Gln Gly Pro Ile Thr Glu Asp
160                 165                 170                 175

Met Leu Cys Ala Gly Tyr Leu Glu Gly Glu Arg Asp Ala Cys Leu Gly
                180                 185                 190

Asp Ser Gly Gly Pro Leu Met Cys Gln Val Asp Gly Ala Trp Leu Leu
            195                 200                 205

Ala Gly Ile Ile Ser Trp Gly Glu Gly Cys Ala Glu Arg Asn Arg Pro
            210                 215                 220

Gly Val Tyr Ile Ser Leu Ser Ala His Arg Ser Trp Val Glu Lys Ile
            225                 230                 235

Val Gln Gly Val Gln Leu Arg Gly Arg Ala Gln Gly Gly Gly Ala Leu
240                 245                 250                 255

Arg Ala Pro Ser Gln Gly Ser Gly Ala Ala Ala Arg Ser
                260                 265
```

<210> SEQ ID NO 3
<211> LENGTH: 1007
<212> TYPE: DNA
<213> ORGANISM: Homo sapiens
<220> FEATURE:
<221> NAME/KEY: CDS
<222> LOCATION: (4)..(960)
<223> OTHER INFORMATION:
<220> FEATURE:
<221> NAME/KEY: mat_peptide
<222> LOCATION: (151)..()
<223> OTHER INFORMATION:

<400> SEQUENCE: 3

```
gcc atg gtg gtt tct gga gcg ccc cca gcc ctg ggt ggg ggc tgt ctc      48
    Met Val Val Ser Gly Ala Pro Pro Ala Leu Gly Gly Gly Cys Leu
```

-continued

```
                   -45                -40                -35
ggc acc ttc acc tcc ctg ctg ctg gcg tcg aca gcc atc ctc aat      96
Gly Thr Phe Thr Ser Leu Leu Leu Ala Ser Thr Ala Ile Leu Asn
                -30                -25                -20 gcg gcc agg ata cct gtt ccc cca gcc tgt ggg aag ccc cag cag ctg  144
Ala Ala Arg Ile Pro Val Pro Pro Ala Cys Gly Lys Pro Gln Gln Leu
            -15                -10                -5 aac cgg gtt gtg ggc ggc gag gac agc act gac agc gag tgc ccc tgg  192
Asn Arg Val Val Gly Gly Glu Asp Ser Thr Asp Ser Glu Trp Pro Trp
 -1  1                   5                      10 atc gtg agc atc cag aag aat ggg acc cac cac tgc gca ggt tct ctg  240
Ile Val Ser Ile Gln Lys Asn Gly Thr His His Cys Ala Gly Ser Leu
 15              20                  25                  30 ctc acc agc cgc tgg gtg atc act gct gcc cac tgt ttc aag gac aac  288
Leu Thr Ser Arg Trp Val Ile Thr Ala Ala His Cys Phe Lys Asp Asn
                 35                  40                  45 ctg aac aaa cca tac ctg ttc tct gtg ctg ctg ggg gcc tgg cag ctg  336
Leu Asn Lys Pro Tyr Leu Phe Ser Val Leu Leu Gly Ala Trp Gln Leu
             50                  55                  60 ggg aac cct ggc tct cgg tcc cag aag gtg ggt gtt gcc tgg gtg gag  384
Gly Asn Pro Gly Ser Arg Ser Gln Lys Val Gly Val Ala Trp Val Glu
         65                  70                  75 ccc cac cct gtg tat tcc tgg aag gaa ggt gcc tgt gca gac att gcc  432
Pro His Pro Val Tyr Ser Trp Lys Glu Gly Ala Cys Ala Asp Ile Ala
     80                  85                  90 ctg gtg cgt ctc gag cgc tcc ata cag ttc tca gag cgg gtc ctg ccc  480
Leu Val Arg Leu Glu Arg Ser Ile Gln Phe Ser Glu Arg Val Leu Pro
 95                 100                 105                 110 atc tgc cta cct gat gcc tct atc cac ctc cct cca aac acc cac tgc  528
Ile Cys Leu Pro Asp Ala Ser Ile His Leu Pro Pro Asn Thr His Cys
                115                 120                 125 tgg atc tca ggc tgg ggg agc atc caa gat gga gtt ccc ttg ccc cac  576
Trp Ile Ser Gly Trp Gly Ser Ile Gln Asp Gly Val Pro Leu Pro His
            130                 135                 140 cct cag acc ctg cag aag ctg aag gtt cct atc atc gac tcg gaa gtc  624
Pro Gln Thr Leu Gln Lys Leu Lys Val Pro Ile Ile Asp Ser Glu Val
        145                 150                 155 tgc agc cat ctg tac tgg cgg gga gca gga cag gga ccc atc act gag  672
Cys Ser His Leu Tyr Trp Arg Gly Ala Gly Gln Gly Pro Ile Thr Glu
    160                 165                 170 gac atg ctg tgt gcc ggc tac ttg gag ggg gag cgg gat gct tgt ctg  720
Asp Met Leu Cys Ala Gly Tyr Leu Glu Gly Glu Arg Asp Ala Cys Leu
175                 180                 185                 190 ggc gac tcc ggg ggc ccc ctc atg tgc cag gtg gac ggc gcc tgg ctg  768
Gly Asp Ser Gly Gly Pro Leu Met Cys Gln Val Asp Gly Ala Trp Leu
                195                 200                 205 ctg gcc ggc atc atc agc tgg ggc gag ggc tgt gcc gag cgc aac agg  816
Leu Ala Gly Ile Ile Ser Trp Gly Glu Gly Cys Ala Glu Arg Asn Arg
            210                 215                 220 ccc ggg gtc tac atc agc ctc tct gcg cac cgc tcc tgg gtg gag aag  864
Pro Gly Val Tyr Ile Ser Leu Ser Ala His Arg Ser Trp Val Glu Lys
        225                 230                 235 atc gtg caa ggg gtg cag ctc cgc ggg cgc gct cag ggg ggt ggg gcc  912
Ile Val Gln Gly Val Gln Leu Arg Gly Arg Ala Gln Gly Gly Gly Ala
    240                 245                 250 ctc agg gca ccg agc cag ggc tct ggg gcc cca gcg ctt ttg tgt ata  960
Leu Arg Ala Pro Ser Gln Gly Ser Gly Ala Pro Ala Leu Leu Cys Ile
255                 260                 265                 270 taaatgttaa tgattttat aggtatttgt aaccctgccc acatatc                1007
```

<210> SEQ ID NO 4
<211> LENGTH: 319
<212> TYPE: PRT
<213> ORGANISM: Homo sapiens

<400> SEQUENCE: 4

```
Met Val Val Ser Gly Ala Pro Pro Ala Leu Gly Gly Cys Leu Gly
            -45                 -40                 -35

Thr Phe Thr Ser Leu Leu Leu Ala Ser Thr Ala Ile Leu Asn Ala
            -30                 -25                 -20

Ala Arg Ile Pro Val Pro Pro Ala Cys Gly Lys Pro Gln Gln Leu Asn
            -15                 -10                  -5

Arg Val Val Gly Gly Glu Asp Ser Thr Asp Ser Glu Trp Pro Trp Ile
 -1   1              5                  10                  15

Val Ser Ile Gln Lys Asn Gly Thr His His Cys Ala Gly Ser Leu Leu
                 20                  25                  30

Thr Ser Arg Trp Val Ile Thr Ala Ala His Cys Phe Lys Asp Asn Leu
             35                  40                  45

Asn Lys Pro Tyr Leu Phe Ser Val Leu Leu Gly Ala Trp Gln Leu Gly
         50                  55                  60

Asn Pro Gly Ser Arg Ser Gln Lys Val Gly Val Ala Trp Val Glu Pro
 65                  70                  75

His Pro Val Tyr Ser Trp Lys Glu Gly Ala Cys Ala Asp Ile Ala Leu
 80                  85                  90                  95

Val Arg Leu Glu Arg Ser Ile Gln Phe Ser Glu Arg Val Leu Pro Ile
                100                 105                 110

Cys Leu Pro Asp Ala Ser Ile His Leu Pro Pro Asn Thr His Cys Trp
                115                 120                 125

Ile Ser Gly Trp Gly Ser Ile Gln Asp Gly Val Pro Leu Pro His Pro
             130                 135                 140

Gln Thr Leu Gln Lys Leu Lys Val Pro Ile Ile Asp Ser Glu Val Cys
145                 150                 155

Ser His Leu Tyr Trp Arg Gly Ala Gly Gln Gly Pro Ile Thr Glu Asp
160                 165                 170                 175

Met Leu Cys Ala Gly Tyr Leu Glu Gly Glu Arg Asp Ala Cys Leu Gly
                180                 185                 190

Asp Ser Gly Gly Pro Leu Met Cys Gln Val Asp Gly Ala Trp Leu Leu
            195                 200                 205

Ala Gly Ile Ile Ser Trp Gly Glu Gly Cys Ala Glu Arg Asn Arg Pro
        210                 215                 220

Gly Val Tyr Ile Ser Leu Ser Ala His Arg Ser Trp Val Glu Lys Ile
    225                 230                 235

Val Gln Gly Val Gln Leu Arg Gly Arg Ala Gln Gly Gly Ala Leu
240                 245                 250                 255

Arg Ala Pro Ser Gln Gly Ser Gly Ala Pro Ala Leu Leu Cys Ile
                260                 265                 270
```

<210> SEQ ID NO 5
<211> LENGTH: 1036
<212> TYPE: DNA
<213> ORGANISM: Homo sapiens
<220> FEATURE:
<221> NAME/KEY: CDS
<222> LOCATION: (4)..(921)
<223> OTHER INFORMATION:
<220> FEATURE:

-continued

<221> NAME/KEY: mat_peptide
<222> LOCATION: (151)..()
<223> OTHER INFORMATION:

<400> SEQUENCE: 5

```
gcc atg gtg gtt tct gga gcg ccc cca gcc ctg ggt ggg ggc tgt ctc       48
    Met Val Val Ser Gly Ala Pro Pro Ala Leu Gly Gly Gly Cys Leu
        -45                 -40                 -35 ggc acc ttc acc tcc ctg ctg ctg ctg gcg tcg aca gcc atc ctc aat       96
Gly Thr Phe Thr Ser Leu Leu Leu Leu Ala Ser Thr Ala Ile Leu Asn
            -30                 -25                 -20 gcg gcc agg ata cct gtt ccc cca gcc tgt ggg aag ccc cag cag ctg      144
Ala Ala Arg Ile Pro Val Pro Pro Ala Cys Gly Lys Pro Gln Gln Leu
        -15                 -10                  -5 aac cgg gtt gtg ggc ggc gag gac agc act gac agc gag tgg ccc tgg      192
Asn Arg Val Val Gly Gly Glu Asp Ser Thr Asp Ser Glu Trp Pro Trp
 -1   1                  5                  10 atc gtg agc atc cag aag aat ggg acc cac cac tgc gca ggt tct ctg      240
Ile Val Ser Ile Gln Lys Asn Gly Thr His His Cys Ala Gly Ser Leu
 15                 20                  25                  30 ctc acc agc cgc tgg gtg atc act gct gcc cac tgt ttc aag gac aac      288
Leu Thr Ser Arg Trp Val Ile Thr Ala Ala His Cys Phe Lys Asp Asn
                 35                  40                  45 ctg aac aaa cca tac ctg ttc tct gtg ctg ctg ggg gcc tgg cag ctg      336
Leu Asn Lys Pro Tyr Leu Phe Ser Val Leu Leu Gly Ala Trp Gln Leu
             50                  55                  60 ggg aac cct ggc tct cgg tcc cag aag gtg ggt gtt gcc tgg gtg gag      384
Gly Asn Pro Gly Ser Arg Ser Gln Lys Val Gly Val Ala Trp Val Glu
         65                  70                  75 ccc cac cct gtg tat tcc tgg aag gaa ggt gcc tgt gca gac att gcc      432
Pro His Pro Val Tyr Ser Trp Lys Glu Gly Ala Cys Ala Asp Ile Ala
     80                  85                  90 ctg gtg cgt ctc gag cgc tcc ata cag ttc tca gag cgg gtc ctg ccc      480
Leu Val Arg Leu Glu Arg Ser Ile Gln Phe Ser Glu Arg Val Leu Pro
 95                 100                 105                 110 atc tgc cta cct gat gcc tct atc cac ctc cct cca aac acc cac tgc      528
Ile Cys Leu Pro Asp Ala Ser Ile His Leu Pro Pro Asn Thr His Cys
                115                 120                 125 tgg atc tca ggc tgg ggg agc atc caa gat gga gtt ccc ttg ccc cac      576
Trp Ile Ser Gly Trp Gly Ser Ile Gln Asp Gly Val Pro Leu Pro His
            130                 135                 140 cct cag acc ctg cag aag ctg aag gtt cct atc atc gac tcg gaa gtc      624
Pro Gln Thr Leu Gln Lys Leu Lys Val Pro Ile Ile Asp Ser Glu Val
        145                 150                 155 tgc agc cat ctg tac tgg cgg gga gca gga cag gga ccc atc act gag      672
Cys Ser His Leu Tyr Trp Arg Gly Ala Gly Gln Gly Pro Ile Thr Glu
160                 165                 170 gac atg ctg tgt gcc ggc tac ttg gag ggg gag cgg gat gct tgt ctg      720
Asp Met Leu Cys Ala Gly Tyr Leu Glu Gly Glu Arg Asp Ala Cys Leu
175                 180                 185                 190 ggc gac tcc ggg ggc ccc ctc atg tgc cag gtg gac ggc gcc tgg ctg      768
Gly Asp Ser Gly Gly Pro Leu Met Cys Gln Val Asp Gly Ala Trp Leu
                195                 200                 205 ctg gcc ggc atc atc agc tgg ggc gag ggc tgt gcc gag cgc aac agg      816
Leu Ala Gly Ile Ile Ser Trp Gly Glu Gly Cys Ala Glu Arg Asn Arg
            210                 215                 220 ccc ggg gtc tac atc agc ctc tct gcg cac cgc tcc tgg gtg gag aag      864
Pro Gly Val Tyr Ile Ser Leu Ser Ala His Arg Ser Trp Val Glu Lys
        225                 230                 235 atc gtg caa ggg gtg cag ctc cgc ggg cgc ccc cgg gcc cca gcg ctt      912
```

-continued

```
Ile Val Gln Gly Val Gln Leu Arg Gly Arg Pro Arg Ala Pro Ala Leu
    240             245                 250
ttg tgt ata taaatgttaa tgattttat aggtatttgt aaccctgccc           961
Leu Cys Ile
255 acatatctta tttattcctc caatttcaat aaattattta ttctccagaa aaaaaaaaaa   1021 aaaaaaaaaa aaaaa                                                   1036

<210> SEQ ID NO 6
<211> LENGTH: 306
<212> TYPE: PRT
<213> ORGANISM: Homo sapiens

<400> SEQUENCE: 6

Met Val Val Ser Gly Ala Pro Pro Ala Leu Gly Gly Cys Leu Gly
                -45             -40             -35

Thr Phe Thr Ser Leu Leu Leu Ala Ser Thr Ala Ile Leu Asn Ala
            -30             -25             -20

Ala Arg Ile Pro Val Pro Pro Ala Cys Gly Lys Pro Gln Gln Leu Asn
        -15             -10              -5

Arg Val Val Gly Gly Glu Asp Ser Thr Asp Ser Glu Trp Pro Trp Ile
-1   1               5              10                  15

Val Ser Ile Gln Lys Asn Gly Thr His His Cys Ala Gly Ser Leu Leu
                20                  25                  30

Thr Ser Arg Trp Val Ile Thr Ala Ala His Cys Phe Lys Asp Asn Leu
            35                  40                  45

Asn Lys Pro Tyr Leu Phe Ser Val Leu Leu Gly Ala Trp Gln Leu Gly
        50                  55                  60

Asn Pro Gly Ser Arg Ser Gln Lys Val Gly Val Ala Trp Val Glu Pro
    65                  70                  75

His Pro Val Tyr Ser Trp Lys Glu Gly Ala Cys Ala Asp Ile Ala Leu
80                  85                  90                  95

Val Arg Leu Glu Arg Ser Ile Gln Phe Ser Glu Arg Val Leu Pro Ile
                100                 105                 110

Cys Leu Pro Asp Ala Ser Ile His Leu Pro Pro Asn Thr His Cys Trp
            115                 120                 125

Ile Ser Gly Trp Gly Ser Ile Gln Asp Gly Val Pro Leu Pro His Pro
        130                 135                 140

Gln Thr Leu Gln Lys Leu Lys Val Pro Ile Ile Asp Ser Glu Val Cys
    145                 150                 155

Ser His Leu Tyr Trp Arg Gly Ala Gly Gln Gly Pro Ile Thr Glu Asp
160                 165                 170                 175

Met Leu Cys Ala Gly Tyr Leu Glu Gly Glu Arg Asp Ala Cys Leu Gly
                180                 185                 190

Asp Ser Gly Gly Pro Leu Met Cys Gln Val Asp Gly Ala Trp Leu Leu
            195                 200                 205

Ala Gly Ile Ile Ser Trp Gly Glu Gly Cys Ala Glu Arg Asn Arg Pro
        210                 215                 220

Gly Val Tyr Ile Ser Leu Ser Ala His Arg Ser Trp Val Glu Lys Ile
    225                 230                 235

Val Gln Gly Val Gln Leu Arg Gly Arg Pro Arg Ala Pro Ala Leu Leu
240                 245                 250                 255

Cys Ile
```

<210> SEQ ID NO 7
<211> LENGTH: 1231
<212> TYPE: DNA
<213> ORGANISM: Homo sapiens
<220> FEATURE:
<221> NAME/KEY: CDS
<222> LOCATION: (4)..(441)
<223> OTHER INFORMATION:
<220> FEATURE:
<221> NAME/KEY: mat_peptide
<222> LOCATION: (151)..()
<223> OTHER INFORMATION:

<400> SEQUENCE: 7

```
gcc atg gtg gtt tct gga gcg ccc cca gcc ctg ggt ggg ggc tgt ctc      48
    Met Val Val Ser Gly Ala Pro Pro Ala Leu Gly Gly Gly Cys Leu
        -45                 -40                 -35 ggc acc ttc acc tcc ctg ctg ctg ctg gcg tcg aca gcc atc ctc aat      96
Gly Thr Phe Thr Ser Leu Leu Leu Leu Ala Ser Thr Ala Ile Leu Asn
            -30                 -25                 -20 gcg gcc agg ata cct gtt ccc cca gcc tgt ggg aag ccc cag cag ctg     144
Ala Ala Arg Ile Pro Val Pro Pro Ala Cys Gly Lys Pro Gln Gln Leu
        -15                 -10                 -5 aac cgg gtt gtg ggc ggc gag gac agc act gac agc gag tgc ccc tgg     192
Asn Arg Val Val Gly Gly Glu Asp Ser Thr Asp Ser Glu Cys Pro Trp
 -1   1               5                  10 atc gtg agc atc cag aag aat ggg acc cac cac tgc gca gga caa cct     240
Ile Val Ser Ile Gln Lys Asn Gly Thr His His Cys Ala Gly Gln Pro
 15                  20                  25                  30 gaa caa acc ata cct gtt ctc tgt gct gct ggg ggc ctg gca gct ggg     288
Glu Gln Thr Ile Pro Val Leu Cys Ala Ala Gly Gly Leu Ala Ala Gly
                 35                  40                  45 gaa ccc tgg ctc tcg gtc cca gaa ggt ggg tgt tgc ctg ggt gga gcc     336
Glu Pro Trp Leu Ser Val Pro Glu Gly Gly Cys Cys Leu Gly Gly Ala
             50                  55                  60 cca ccc tgt gta ttc ctg gaa gga agg tgc ctg tgc aga cat tgc cct     384
Pro Pro Cys Val Phe Leu Glu Gly Arg Cys Leu Cys Arg His Cys Pro
         65                  70                  75 ggt gcg tct cga gcg ctc cat aca gtt ctc aga gcg ggt cct gcc cat     432
Gly Ala Ser Arg Ala Leu His Thr Val Leu Arg Ala Gly Pro Ala His
     80                  85                  90 ctg cct acc tgatgcctct tccacctccc tccaaacacc cactgctgga             481
Leu Pro Thr
95 tctcaggctg ggggagcatc caagatggag ttcccttgcc ccaccctcag accctgcaga    541 agctgaaggt tcctatcatc gactcggaag tctgcagcca tctgtactgg cggggagcag    601 gacaggggacc catcactgag gacatgctgt gtgccggcta cttggagggg gagcgggatg   661 cttgtctggg cgactccggg ggccccctca tgtgccaggt ggacggcgcc tggctgctgg    721 ccggcatcat cagctgggc gagggctgtg ccgagcgcaa caggcccggg gtctacatca     781 gcctctctgc gcaccgctcc tggtggaga agatcgtgca agggggtgcag ctccgcgggc    841 gcgctcaggg gggtggggcc ctcagggcac cgagccaggg ctctgggcc gccgcgcgct     901 cctagggcgc agcgggacgc ggggctcgga tctgaaaggc ggccagatcc acatctggat    961 ctggatctgc ggcggcctcg gcggttttcc ccgccgtaa ataggctcat ctacctctac    1021 ctctgggggc ccggacggct gctgcggaaa ggaaaccccc tccccgaccc gcccgacggc    1081 ctcaggcccc gccctccaag gcatcaggcc ccgcccaacg gcctcatgtc cccgcccca    1141 cgacttccgg ccccgccccc gggccccagc gcttttgtgt atataaatgt taatgatttt   1201
```

```
tataggtatt tgtaaccctg cccacatatc                                         1231
```

<210> SEQ ID NO 8
<211> LENGTH: 146
<212> TYPE: PRT
<213> ORGANISM: Homo sapiens

<400> SEQUENCE: 8

```
Met Val Val Ser Gly Ala Pro Pro Ala Leu Gly Gly Gly Cys Leu Gly
                -45                 -40                 -35

Thr Phe Thr Ser Leu Leu Leu Leu Ala Ser Thr Ala Ile Leu Asn Ala
            -30                 -25                 -20

Ala Arg Ile Pro Val Pro Pro Ala Cys Gly Lys Pro Gln Gln Leu Asn
        -15                 -10                 -5

Arg Val Val Gly Gly Glu Asp Ser Thr Asp Ser Glu Trp Pro Trp Ile
-1   1               5                  10                 15

Val Ser Ile Gln Lys Asn Gly Thr His His Cys Ala Gly Gln Pro Glu
                20                 25                 30

Gln Thr Ile Pro Val Leu Cys Ala Ala Gly Gly Leu Ala Ala Gly Glu
                35                 40                 45

Pro Trp Leu Ser Val Pro Glu Gly Gly Cys Cys Leu Gly Gly Ala Pro
            50                 55                 60

Pro Cys Val Phe Leu Glu Gly Arg Cys Leu Cys Arg His Cys Pro Gly
    65                 70                 75

Ala Ser Arg Ala Leu His Thr Val Leu Arg Ala Gly Pro Ala His Leu
80                 85                 90                 95

Pro Thr
```

<210> SEQ ID NO 9
<211> LENGTH: 952
<212> TYPE: DNA
<213> ORGANISM: Homo sapiens
<220> FEATURE:
<221> NAME/KEY: CDS
<222> LOCATION: (4)..(624)
<223> OTHER INFORMATION:
<220> FEATURE:
<221> NAME/KEY: mat_peptide
<222> LOCATION: (151)..()
<223> OTHER INFORMATION:

<400> SEQUENCE: 9

```
gcc atg gtg gtt tct gga gcg ccc cca gcc ctg ggt ggg ggc tgt ctc         48
    Met Val Val Ser Gly Ala Pro Pro Ala Leu Gly Gly Gly Cys Leu
        -45                 -40                 -35 ggc acc ttc acc tcc ctg ctg ctg ctg gcg tcg aca gcc atc ctc aat         96
Gly Thr Phe Thr Ser Leu Leu Leu Leu Ala Ser Thr Ala Ile Leu Asn
            -30                 -25                 -20 gcg gcc agg ata cct gtt ccc cca gcc tgt ggg aag ccc cag cag ctg        144
Ala Ala Arg Ile Pro Val Pro Pro Ala Cys Gly Lys Pro Gln Gln Leu
        -15                 -10                 -5 aac cgg gtt gtg ggc ggc gag gac agc act gac agc gag tgg ccc tgg        192
Asn Arg Val Val Gly Gly Glu Asp Ser Thr Asp Ser Glu Trp Pro Trp
        -1  1               5                   10 atc gtg agc atc cag aag aat ggg acc cac cac tgc gca gtt ccc ttg        240
Ile Val Ser Ile Gln Lys Asn Gly Thr His His Cys Ala Val Pro Leu
 15                 20                  25                  30 ccc cac cct cag acc ctg cag aag ctg aag gtt cct atc atc gac tcg        288
Pro His Pro Gln Thr Leu Gln Lys Leu Lys Val Pro Ile Ile Asp Ser
                35                  40                  45
```

-continued

```
gaa gtc tgc agc cat ctg tac tgg cgg gga gca gga cag gga ccc atc     336
Glu Val Cys Ser His Leu Tyr Trp Arg Gly Ala Gly Gln Gly Pro Ile
         50                  55                  60 act gag gac atg ctg tgt gcc ggc tac ttg gag ggg gag cgg gat gct     384
Thr Glu Asp Met Leu Cys Ala Gly Tyr Leu Glu Gly Glu Arg Asp Ala
 65                  70                  75 tgt ctg ggc gac tcc ggg ggc ccc ctc atg tgc cag gtg gac ggc gcc     432
Cys Leu Gly Asp Ser Gly Gly Pro Leu Met Cys Gln Val Asp Gly Ala
         80                  85                  90 tgg ctg ctg gcc ggc atc atc agc tgg ggc gag ggc tgt gcc gag cgc     480
Trp Leu Leu Ala Gly Ile Ile Ser Trp Gly Glu Gly Cys Ala Glu Arg
 95                 100                 105                 110 aac agg ccc ggg gtc tac atc agc ctc tct gcg cac cgc tcc tgg gtg     528
Asn Arg Pro Gly Val Tyr Ile Ser Leu Ser Ala His Arg Ser Trp Val
                    115                 120                 125 gag aag atc gtg caa ggg gtg cag ctc cgc ggg cgc gct cag ggg ggt     576
Glu Lys Ile Val Gln Gly Val Gln Leu Arg Gly Arg Ala Gln Gly Gly
                130                 135                 140 ggg gcc ctc agg gca ccg agc cag ggc tct ggg gcc gcc gcg cgc tcc     624
Gly Ala Leu Arg Ala Pro Ser Gln Gly Ser Gly Ala Ala Ala Arg Ser
        145                 150                 155 tagggcgcag cgggacgcgg ggctcggatc tgaaaggcgg ccagatccac atctggatct   684
ggatctgcgg cggcctcggg cggtttcccc cgccgtaaat aggctcatct acctctacct   744
ctgggggccc ggacggctgc tgcggaaagg aaacccccctc cccgaccgc ccgacggcct   804 caggccccgc cctccaaggc atcaggcccc gcccaacggc ctcatgtccc cgccccacg    864 acttccggcc ccgcccccgg ccccagcgc ttttgtgtat ataaatgtta atgattttta    924
taggtatttg taaccctgcc cacatatc                                      952
```

<210> SEQ ID NO 10
<211> LENGTH: 207
<212> TYPE: PRT
<213> ORGANISM: Homo sapiens

<400> SEQUENCE: 10

```
Met Val Val Ser Gly Ala Pro Pro Ala Leu Gly Gly Cys Leu Gly
                -45                 -40                 -35

Thr Phe Thr Ser Leu Leu Leu Ala Ser Thr Ala Ile Leu Asn Ala
            -30                 -25                 -20

Ala Arg Ile Pro Val Pro Pro Ala Cys Gly Lys Pro Gln Gln Leu Asn
        -15                 -10                  -5

Arg Val Val Gly Gly Glu Asp Ser Thr Asp Ser Glu Trp Pro Trp Ile
 -1   1              5                  10                  15

Val Ser Ile Gln Lys Asn Gly Thr His His Cys Ala Val Pro Leu Pro
                 20                  25                  30

His Pro Gln Thr Leu Gln Lys Leu Lys Val Pro Ile Ile Asp Ser Glu
         35                  40                  45

Val Cys Ser His Leu Tyr Trp Arg Gly Ala Gly Gln Gly Pro Ile Thr
         50                  55                  60

Glu Asp Met Leu Cys Ala Gly Tyr Leu Glu Gly Glu Arg Asp Ala Cys
 65                  70                  75

Leu Gly Asp Ser Gly Gly Pro Leu Met Cys Gln Val Asp Gly Ala Trp
         80                  85                  90                  95

Leu Leu Ala Gly Ile Ile Ser Trp Gly Glu Gly Cys Ala Glu Arg Asn
                100                 105                 110

Arg Pro Gly Val Tyr Ile Ser Leu Ser Ala His Arg Ser Trp Val Glu
```

115                 120                 125
Lys Ile Val Gln Gly Val Gln Leu Arg Gly Arg Ala Gln Gly Gly
            130                 135                 140

Ala Leu Arg Ala Pro Ser Gln Gly Ser Gly Ala Ala Ala Arg Ser
    145                 150                 155

<210> SEQ ID NO 11
<211> LENGTH: 1083
<212> TYPE: DNA
<213> ORGANISM: Homo sapiens
<220> FEATURE:
<221> NAME/KEY: CDS
<222> LOCATION: (4)..(396)
<223> OTHER INFORMATION:
<220> FEATURE:
<221> NAME/KEY: mat_peptide
<222> LOCATION: (151)..()
<223> OTHER INFORMATION:

<400> SEQUENCE: 11

| | |
|---|---:|
| gcc atg gtg gtt tct gga gcg ccc cca gcc ctg ggt ggg ggc tgt ctc<br>    Met Val Val Ser Gly Ala Pro Pro Ala Leu Gly Gly Gly Cys Leu<br>                        -45                     -40                  -35 | 48 |
| ggc acc ttc acc tcc ctg ctg ctg ctg gcg tcg aca gcc atc ctc aat<br>Gly Thr Phe Thr Ser Leu Leu Leu Leu Ala Ser Thr Ala Ile Leu Asn<br>             -30                  -25                  -20 | 96 |
| gcg gcc agg ata cct gtt ccc cca gcc tgt ggg aag ccc cag cag ctg<br>Ala Ala Arg Ile Pro Val Pro Pro Ala Cys Gly Lys Pro Gln Gln Leu<br>         -15                  -10                  -5 | 144 |
| aac cgg gtt gtg ggc ggc gag gac agc act gac agc gag tgg ccc tgg<br>Asn Arg Val Val Gly Gly Glu Asp Ser Thr Asp Ser Glu Trp Pro Trp<br>    -1  1                5                      10 | 192 |
| atc gtg agc atc cag aag aat ggg acc cac cac tgc gca ggt tct ctg<br>Ile Val Ser Ile Gln Lys Asn Gly Thr His His Cys Ala Gly Ser Leu<br>15             20                  25                  30 | 240 |
| ctc acc agc cgc tgg gtg atc act gct gcc cac tgt ttc aag gac aac<br>Leu Thr Ser Arg Trp Val Ile Thr Ala Ala His Cys Phe Lys Asp Asn<br>             35                  40                  45 | 288 |
| ctg aac aaa cca tac ctg ttc tct gtg ctg ctg ggg gcc tgg cag ctg<br>Leu Asn Lys Pro Tyr Leu Phe Ser Val Leu Leu Gly Ala Trp Gln Leu<br>         50                  55                  60 | 336 |
| ggg aac cct ggc tct cgg tcc cag aag ttc cct tgc ccc acc ctc aga<br>Gly Asn Pro Gly Ser Arg Ser Gln Lys Phe Pro Cys Pro Thr Leu Arg<br>       65                  70                  75 | 384 |
| ccc tgc aga agc tgaaggttcc tatcatcgac tcggaagtct gcagccatct<br>Pro Cys Arg Ser<br>         80 | 436 |
| gtactggcgg ggagcaggac agggacccat cactgaggac atgctgtgtg ccggctactt | 496 |
| ggaggggggag cgggatgctt gtctggcgga ctccgggggc ccctcatgt gccaggtgga | 556 |
| cggcgcctgg ctgctggccg gcatcatcag ctggggcgag ggctgtgccg agcgcaacag | 616 |
| gcccggggtc tacatcagcc tctctgcgca ccgctcctgg gtggagaaga tcgtgcaagg | 676 |
| ggtgcagctc cgcgggcgcg ctcagggggg tgggccctc agggcaccga gccagggctc | 736 |
| tggggccgcc gcgcgctcct agggcgcagc gggacgcggg gctcggatct gaaaggcggc | 796 |
| cagatccaca tctggatctg gatctgcggc ggcctcgggc ggtttccccc gccgtaaata | 856 |
| ggctcatcta cctctaccct tgggggcccg gacggctgct gcggaaagga aaccccctcc | 916 |
| ccgaccgcc cgacgcctc aggccccgcc tccaaggca tcaggcccg cccaacggcc | 976 |
| tcatgtcccc gcccccacga cttccggccc cgccccgggg cccagcgct tttgtgtata | 1036 |

```
taaatgttaa tgatttttat aggtatttgt aaccctgccc acatatc                    1083
```

```
<210> SEQ ID NO 12
<211> LENGTH: 131
<212> TYPE: PRT
<213> ORGANISM: Homo sapiens

<400> SEQUENCE: 12
```

```
Met Val Val Ser Gly Ala Pro Pro Ala Leu Gly Gly Gly Cys Leu Gly
                -45                 -40                 -35

Thr Phe Thr Ser Leu Leu Leu Leu Ala Ser Thr Ala Ile Leu Asn Ala
            -30                 -25                 -20

Ala Arg Ile Pro Val Pro Pro Ala Cys Gly Lys Pro Gln Gln Leu Asn
        -15                 -10                  -5

Arg Val Val Gly Gly Glu Asp Ser Thr Asp Ser Glu Trp Pro Trp Ile
 -1   1               5                  10                  15

Val Ser Ile Gln Lys Asn Gly Thr His His Cys Ala Gly Ser Leu Leu
                 20                  25                  30

Thr Ser Arg Trp Val Ile Thr Ala Ala His Cys Phe Lys Asp Asn Leu
             35                  40                  45

Asn Lys Pro Tyr Leu Phe Ser Val Leu Leu Gly Ala Trp Gln Leu Gly
         50                  55                  60

Asn Pro Gly Ser Arg Ser Gln Lys Phe Pro Cys Pro Thr Leu Arg Pro
     65                  70                  75

Cys Arg Ser
 80
```

```
<210> SEQ ID NO 13
<211> LENGTH: 723
<212> TYPE: DNA
<213> ORGANISM: Homo sapiens
<220> FEATURE:
<221> NAME/KEY: CDS
<222> LOCATION: (4)..(705)
<223> OTHER INFORMATION:
<220> FEATURE:
<221> NAME/KEY: mat_peptide
<222> LOCATION: (151)..()
<223> OTHER INFORMATION:

<400> SEQUENCE: 13
```

```
gcc atg gtg gtt tct gga gcg ccc cca gcc ctg ggt ggg ggc tgt ctc       48
    Met Val Val Ser Gly Ala Pro Pro Ala Leu Gly Gly Gly Cys Leu
                    -45                 -40                 -35 ggc acc ttc acc tcc ctg ctg ctg ctg gcg tcg aca gcc atc ctc aat       96
Gly Thr Phe Thr Ser Leu Leu Leu Leu Ala Ser Thr Ala Ile Leu Asn
                -30                 -25                 -20 gcg gcc agg ata cct gtt ccc cca gcc tgt ggg aag ccc cag cag ctg      144
Ala Ala Arg Ile Pro Val Pro Pro Ala Cys Gly Lys Pro Gln Gln Leu
            -15                 -10                  -5 aac cgg gtt gtg ggc ggc gag gac agc act gac agc gag tgg ccc tgg      192
Asn Arg Val Val Gly Gly Glu Asp Ser Thr Asp Ser Glu Trp Pro Trp
         -1   1               5                  10 atc gtg agc atc cag aag aat ggg acc cac cac tgc gca ggt tct ctg      240
Ile Val Ser Ile Gln Lys Asn Gly Thr His His Cys Ala Gly Ser Leu
 15                  20                  25                  30 ctc acc agc cgc tgg gtg atc act gct gcc cac tgt ttc aag gac aac      288
Leu Thr Ser Arg Trp Val Ile Thr Ala Ala His Cys Phe Lys Asp Asn
                 35                  40                  45 ctg aac aaa cca tac ctg ttc tct gtg ctg ctg ggg gcc tgg cag ctg      336
```

| | | |
|---|---|---|
| Leu Asn Lys Pro Tyr Leu Phe Ser Val Leu Leu Gly Ala Trp Gln Leu<br>            50                        55                        60 | | |

```
ggg aac cct ggc tct cgg tcc cag aag gtg ggt gtt gcc tgg gtg gag    384
Gly Asn Pro Gly Ser Arg Ser Gln Lys Val Gly Val Ala Trp Val Glu
         65                  70                  75 ccc cac cct gtg tat tcc tgg aag gaa ggt gcc tgt gca gac att gcc    432
Pro His Pro Val Tyr Ser Trp Lys Glu Gly Ala Cys Ala Asp Ile Ala
     80                  85                  90 ctg gtg cgt ctc gag cgc tcc ata cag ttc tca gag cgg gtc ctg ccc    480
Leu Val Arg Leu Glu Arg Ser Ile Gln Phe Ser Glu Arg Val Leu Pro
 95                 100                 105                 110 atc tgc cta cct gat gcc tct atc cac ctc cct cca aac acc cac tgc    528
Ile Cys Leu Pro Asp Ala Ser Ile His Leu Pro Pro Asn Thr His Cys
                115                 120                 125 tgg atc tca ggc tgg ggg agc atc caa gat gga gtt ccc ttg ccc cac    576
Trp Ile Ser Gly Trp Gly Ser Ile Gln Asp Gly Val Pro Leu Pro His
            130                 135                 140 cct cag acc ctc tcc aag gca tca ggc ccc gcc caa cgg cct cat gtc    624
Pro Gln Thr Leu Ser Lys Ala Ser Gly Pro Ala Gln Arg Pro His Val
        145                 150                 155 ccc gcc ccc acg act tcc ggc ccc gcc ccg ggc ccc agc gct ttt gtg    672
Pro Ala Pro Thr Thr Ser Gly Pro Ala Pro Gly Pro Ser Ala Phe Val
    160                 165                 170 tat ata aat gtt aat gat ttt tat agg tat ttg taaccctgcc cacatatc   723
Tyr Ile Asn Val Asn Asp Phe Tyr Arg Tyr Leu
175                 180                 185

<210> SEQ ID NO 14
<211> LENGTH: 234
<212> TYPE: PRT
<213> ORGANISM: Homo sapiens

<400> SEQUENCE: 14

Met Val Val Ser Gly Ala Pro Pro Ala Leu Gly Gly Cys Leu Gly
            -45                 -40                 -35

Thr Phe Thr Ser Leu Leu Leu Leu Ala Ser Thr Ala Ile Leu Asn Ala
        -30                 -25                 -20

Ala Arg Ile Pro Val Pro Pro Ala Cys Gly Lys Pro Gln Gln Leu Asn
    -15                 -10                  -5

Arg Val Val Gly Gly Glu Asp Ser Thr Asp Ser Glu Trp Pro Trp Ile
 -1   1                   5                  10                  15

Val Ser Ile Gln Lys Asn Gly Thr His His Cys Ala Gly Ser Leu Leu
                 20                  25                  30

Thr Ser Arg Trp Val Ile Thr Ala Ala His Cys Phe Lys Asp Asn Leu
             35                  40                  45

Asn Lys Pro Tyr Leu Phe Ser Val Leu Leu Gly Ala Trp Gln Leu Gly
         50                  55                  60

Asn Pro Gly Ser Arg Ser Gln Lys Val Gly Val Ala Trp Val Glu Pro
     65                  70                  75

His Pro Val Tyr Ser Trp Lys Glu Gly Ala Cys Ala Asp Ile Ala Leu
 80                  85                  90                  95

Val Arg Leu Glu Arg Ser Ile Gln Phe Ser Glu Arg Val Leu Pro Ile
                100                 105                 110

Cys Leu Pro Asp Ala Ser Ile His Leu Pro Pro Asn Thr His Cys Trp
            115                 120                 125

Ile Ser Gly Trp Gly Ser Ile Gln Asp Gly Val Pro Leu Pro His Pro
        130                 135                 140
```

-continued

```
Gln Thr Leu Ser Lys Ala Ser Gly Pro Ala Gln Arg Pro His Val Pro
    145                 150                 155
Ala Pro Thr Thr Ser Gly Pro Ala Pro Gly Pro Ser Ala Phe Val Tyr
160                 165                 170                 175
Ile Asn Val Asn Asp Phe Tyr Arg Tyr Leu
                180                 185

<210> SEQ ID NO 15
<211> LENGTH: 1004
<212> TYPE: DNA
<213> ORGANISM: Homo sapiens
<220> FEATURE:
<221> NAME/KEY: CDS
<222> LOCATION: (4)..(390)
<223> OTHER INFORMATION:
<220> FEATURE:
<221> NAME/KEY: mat_peptide
<222> LOCATION: (151)..()
<223> OTHER INFORMATION:

<400> SEQUENCE: 15 gcc atg gtg gtt tct gga gcg ccc cca gcc ctg ggt ggg ggc tgt ctc      48
    Met Val Val Ser Gly Ala Pro Pro Ala Leu Gly Gly Gly Cys Leu
        -45                 -40                 -35 ggc acc ttc acc tcc ctg ctg ctg ctg gcg tcg aca gcc atc ctc aat      96
Gly Thr Phe Thr Ser Leu Leu Leu Leu Ala Ser Thr Ala Ile Leu Asn
            -30                 -25                 -20 gcg gcc agg ata cct gtt ccc cca gcc tgt ggg aag ccc cag cag ctg     144
Ala Ala Arg Ile Pro Val Pro Pro Ala Cys Gly Lys Pro Gln Gln Leu
        -15                 -10                 -5 aac cgg gtt gtg ggc ggc gag gac agc act gac agc gag tgg ccc tgg     192
Asn Arg Val Val Gly Gly Glu Asp Ser Thr Asp Ser Glu Trp Pro Trp
 -1  1               5                  10 atc gtg agc atc cag aag aat ggg acc cac cac tgc gca ggt tct ctg     240
Ile Val Ser Ile Gln Lys Asn Gly Thr His His Cys Ala Gly Ser Leu
15                  20                  25                  30 ctc acc agc cgc tgg gtg atc act gct gcc cac tgt ttc aag gat tcc     288
Leu Thr Ser Arg Trp Val Ile Thr Ala Ala His Cys Phe Lys Asp Ser
                35                  40                  45 ctt gcc cca ccc tca gac cct gca gaa gct gaa ggt tcc tat cat cga     336
Leu Ala Pro Pro Ser Asp Pro Ala Glu Ala Glu Gly Ser Tyr His Arg
            50                  55                  60 ctc gga agt ctg cag cca tct gta ctg gcg ggg agc agg aca ggg acc     384
Leu Gly Ser Leu Gln Pro Ser Val Leu Ala Gly Ser Arg Thr Gly Thr
        65                  70                  75 cat cac tgaggacatg ctgtgtgccg gctacttgga gggggagcgg gatgcttgtc      440
His His
    80 tgggcgactc cggggcccc ctcatgtgcc aggtggacgg cgcctggctg ctggccggca     500 tcatcagctg gggcgagggc tgtgccgagc gcaacaggcc cggggtctac atcagcctct     560 ctgcgcaccg ctcctgggtg agaagatcg tgcaagggt gcagctccgc gggcgcgctc       620 agggggtgtgg ggccctcagg gcaccgagcc agggctctgg ggccgccgcg cgctcctagg     680 gcgcagcggg acgcggggct cggatctgaa aggcggccag atccacatct ggatctggat      740 ctgcggcggc ctcgggcggt tccccccgcc gtaaataggc tcatctacct ctacctctgg     800 gggcccggac ggctgctgcg gaaaggaaac ccctccccg accogccga cggcctcagg       860 ccccgccctc caaggcatca ggccccgccc aacggcctca tgtccccgcc ccacgactt     920 ccggcccgc ccccgggccc cagcgctttt gtgtatataa atgttaatga tttttatagg   980
```
tatttgtaac cctgcccaca tatc                                              1004

<210> SEQ ID NO 16
<211> LENGTH: 129
<212> TYPE: PRT
<213> ORGANISM: Homo sapiens

<400> SEQUENCE: 16

Met Val Val Ser Gly Ala Pro Pro Ala Leu Gly Gly Gly Cys Leu Gly
                -45                 -40                 -35

Thr Phe Thr Ser Leu Leu Leu Leu Ala Ser Thr Ala Ile Leu Asn Ala
            -30                 -25                 -20

Ala Arg Ile Pro Val Pro Pro Ala Cys Gly Lys Pro Gln Gln Leu Asn
        -15                 -10                  -5

Arg Val Val Gly Gly Glu Asp Ser Thr Asp Ser Glu Trp Pro Trp Ile
 -1   1              5                  10                  15

Val Ser Ile Gln Lys Asn Gly Thr His His Cys Ala Gly Ser Leu Leu
                 20                  25                  30

Thr Ser Arg Trp Val Ile Thr Ala Ala His Cys Phe Lys Asp Ser Leu
             35                  40                  45

Ala Pro Pro Ser Asp Pro Ala Glu Ala Glu Gly Ser Tyr His Arg Leu
         50                  55                  60

Gly Ser Leu Gln Pro Ser Val Leu Ala Gly Ser Arg Thr Gly Thr His
     65                  70                  75

His
 80

<210> SEQ ID NO 17
<211> LENGTH: 948
<212> TYPE: DNA
<213> ORGANISM: Homo sapiens
<220> FEATURE:
<221> NAME/KEY: CDS
<222> LOCATION: (4)..(909)
<223> OTHER INFORMATION:
<220> FEATURE:
<221> NAME/KEY: mat_peptide
<222> LOCATION: (151)..()
<223> OTHER INFORMATION:

<400> SEQUENCE: 17 gcc atg gtg gtt tct gga gcg ccc cca gcc ctg ggt ggg ggc tgt ctc      48
    Met Val Val Ser Gly Ala Pro Pro Ala Leu Gly Gly Gly Cys Leu
        -45                 -40                 -35 ggc acc ttc acc tcc ctg ctg ctg ctg gcg tcg aca gcc atc ctc aat      96
Gly Thr Phe Thr Ser Leu Leu Leu Leu Ala Ser Thr Ala Ile Leu Asn
            -30                 -25                 -20 gcg gcc agg ata cct gtt ccc cca gcc tgt ggg aag ccc cag cag ctg     144
Ala Ala Arg Ile Pro Val Pro Pro Ala Cys Gly Lys Pro Gln Gln Leu
        -15                 -10                  -5 aac cgg gtt gtg ggc ggc gag gac agc act gac agc gag tgg ccc tgg     192
Asn Arg Val Val Gly Gly Glu Asp Ser Thr Asp Ser Glu Trp Pro Trp
 -1   1              5                  10 atc gtg agc atc cag aag aat ggg acc cac cac tgc gca ggt tct ctg     240
Ile Val Ser Ile Gln Lys Asn Gly Thr His His Cys Ala Gly Ser Leu
 15                  20                  25                  30 ctc acc agc cgc tgg gtg atc act gct gcc cac tgt ttc aag gac aac     288
Leu Thr Ser Arg Trp Val Ile Thr Ala Ala His Cys Phe Lys Asp Asn
                 35                  40                  45 ctg aac aaa cca tac ctg ttc tct gtg ctg ctg ggg gcc tgg cag ctg     336
Leu Asn Lys Pro Tyr Leu Phe Ser Val Leu Leu Gly Ala Trp Gln Leu

```
                     50                  55                  60
ggg aac cct ggc tct cgg tcc cag aaa gtg ggt gtt gcc tgg gtg gag    384
Gly Asn Pro Gly Ser Arg Ser Gln Lys Val Gly Val Ala Trp Val Glu
             65                  70                  75 ccc cac cct gtg tat tcc tgg aag gaa ggt gcc tgt gca gac att gcc    432
Pro His Pro Val Tyr Ser Trp Lys Glu Gly Ala Cys Ala Asp Ile Ala
 80                  85                  90 ctg gtg cgt ctc gag cgc tcc ata cag ttc tca gag cgg gtc ctg ccc    480
Leu Val Arg Leu Glu Arg Ser Ile Gln Phe Ser Glu Arg Val Leu Pro
 95                 100                 105                 110 atc tgc cta cct gat gcc tct atc cac ctc cct cca aac acc cac tgc    528
Ile Cys Leu Pro Asp Ala Ser Ile His Leu Pro Pro Asn Thr His Cys
                115                 120                 125 tgg atc tca ggc tgg ggg agc atc caa gat gga gtt ccc ttg ccc cac    576
Trp Ile Ser Gly Trp Gly Ser Ile Gln Asp Gly Val Pro Leu Pro His
            130                 135                 140 cct cag acc ctg cag aag ctg aag gtt cct atc atc gac tcg gaa gtc    624
Pro Gln Thr Leu Gln Lys Leu Lys Val Pro Ile Ile Asp Ser Glu Val
        145                 150                 155 tgc agc cat ctg tac tgg cgg gga gca gga cag gga ccc atc act gag    672
Cys Ser His Leu Tyr Trp Arg Gly Ala Gly Gln Gly Pro Ile Thr Glu
    160                 165                 170 gac atg ctg tgt gcc ggc tac ttg gag ggg gag cgg gat gct tgt ctg    720
Asp Met Leu Cys Ala Gly Tyr Leu Glu Gly Glu Arg Asp Ala Cys Leu
175                 180                 185                 190 gtg agc tcc ctc gag ccc ccc acc cct ggc cag gag ggc ctc ggg aag    768
Val Ser Ser Leu Glu Pro Pro Thr Pro Gly Gln Glu Gly Leu Gly Lys
                195                 200                 205 gag cca gcg tca gtc ctg tcc cca ctg agc ccc aca acc tct ccc tgg    816
Glu Pro Ala Ser Val Leu Ser Pro Leu Ser Pro Thr Thr Ser Pro Trp
            210                 215                 220 cct cct ccc cag aac tgg ctg tgc ctg aca gtc ccg ggt ccc cat aga    864
Pro Pro Pro Gln Asn Trp Leu Cys Leu Thr Val Pro Gly Pro His Arg
        225                 230                 235 acc agc ctc agc ctg gct cag cca ctc act tat ttg ttc aga cat        909
Thr Ser Leu Ser Leu Ala Gln Pro Leu Thr Tyr Leu Phe Arg His
    240                 245                 250 taaactgggc atcccagctg caaaaaaaaa aaaaaaaa                          948

<210> SEQ ID NO 18
<211> LENGTH: 302
<212> TYPE: PRT
<213> ORGANISM: Homo sapiens

<400> SEQUENCE: 18

Met Val Val Ser Gly Ala Pro Ala Leu Gly Gly Cys Leu Gly
            -45                 -40                 -35

Thr Phe Thr Ser Leu Leu Leu Ala Ser Thr Ala Ile Leu Asn Ala
            -30                 -25                 -20

Ala Arg Ile Pro Val Pro Pro Ala Cys Gly Lys Pro Gln Gln Leu Asn
        -15                 -10                  -5

Arg Val Val Gly Gly Glu Asp Ser Thr Asp Ser Glu Trp Pro Trp Ile
 -1  1                   5                  10                  15

Val Ser Ile Gln Lys Asn Gly Thr His His Cys Ala Gly Ser Leu Leu
                20                  25                  30

Thr Ser Arg Trp Val Ile Thr Ala Ala His Cys Phe Lys Asp Asn Leu
            35                  40                  45

Asn Lys Pro Tyr Leu Phe Ser Val Leu Leu Gly Ala Trp Gln Leu Gly
```

-continued

```
                 50                  55                  60
Asn Pro Gly Ser Arg Ser Gln Lys Val Gly Val Ala Trp Val Glu Pro
             65                  70                  75

His Pro Val Tyr Ser Trp Lys Glu Gly Ala Cys Ala Asp Ile Ala Leu
 80                  85                  90                  95

Val Arg Leu Glu Arg Ser Ile Gln Phe Ser Glu Arg Val Leu Pro Ile
                100                 105                 110

Cys Leu Pro Asp Ala Ser Ile His Leu Pro Pro Asn Thr His Cys Trp
            115                 120                 125

Ile Ser Gly Trp Gly Ser Ile Gln Asp Gly Val Pro Leu Pro His Pro
            130                 135                 140

Gln Thr Leu Gln Lys Leu Lys Val Pro Ile Ile Asp Ser Glu Val Cys
    145                 150                 155

Ser His Leu Tyr Trp Arg Gly Ala Gly Gln Gly Pro Ile Thr Glu Asp
160                 165                 170                 175

Met Leu Cys Ala Gly Tyr Leu Glu Gly Glu Arg Asp Ala Cys Leu Val
                180                 185                 190

Ser Ser Leu Glu Pro Pro Thr Pro Gly Gln Glu Gly Leu Gly Lys Glu
            195                 200                 205

Pro Ala Ser Val Leu Ser Pro Leu Ser Pro Thr Thr Ser Pro Trp Pro
            210                 215                 220

Pro Pro Gln Asn Trp Leu Cys Leu Thr Val Pro Gly Pro His Arg Thr
    225                 230                 235

Ser Leu Ser Leu Ala Gln Pro Leu Thr Tyr Leu Phe Arg His
240                 245                 250

<210> SEQ ID NO 19
<211> LENGTH: 1322
<212> TYPE: DNA
<213> ORGANISM: Mus. Sp.
<220> FEATURE:
<221> NAME/KEY: CDS
<222> LOCATION: (80)..(1003)
<223> OTHER INFORMATION:
<220> FEATURE:
<221> NAME/KEY: mat_peptide
<222> LOCATION: (227)..()
<223> OTHER INFORMATION:

<400> SEQUENCE: 19
cctgccagtc tcaagcaaca cagcccttag gtcctttgag ccggccagca gccttgctgg      60
gtctccaccc ataccagca atg atg atc tcc aga cct ccc cca gca ctg ggt     112
                      Met Met Ile Ser Arg Pro Pro Ala Leu Gly
                                   -45                 -40 ggg gac cag ttc agc atc tta atc ctt ctg gtg ctg ctg act tcc aca     160
Gly Asp Gln Phe Ser Ile Leu Ile Leu Leu Val Leu Leu Thr Ser Thr
            -35                 -30                 -25 gct ccc atc agt gct gcc acc atc cga gtg tcc cca gac tgt ggg aag     208
Ala Pro Ile Ser Ala Ala Thr Ile Arg Val Ser Pro Asp Cys Gly Lys
        -20                 -15                 -10 cct cag cag ctg aac cgg att gtg gga ggt gag gac agc atg gat gcc     256
Pro Gln Gln Leu Asn Arg Ile Val Gly Gly Glu Asp Ser Met Asp Ala
     -5                  -1  1                   5                  10 cag tgg ccc tgg att gtt agc atc ctc aag aat ggc tcc cac cac tgt     304
Gln Trp Pro Trp Ile Val Ser Ile Leu Lys Asn Gly Ser His His Cys
                 15                  20                  25 gca ggc tcc ctg ctc acc aac cgc tgg gtg gtc aca gcc gcg cac tgc     352
Ala Gly Ser Leu Leu Thr Asn Arg Trp Val Val Thr Ala Ala His Cys
             30                  35                  40
```

```
ttt aag agc aat atg gac aaa cca tct ctg ttc tca gta ttg ttg ggg     400
Phe Lys Ser Asn Met Asp Lys Pro Ser Leu Phe Ser Val Leu Leu Gly
            45                  50                  55 gcc tgg aag ctg ggg agc cca ggc cca agg tcc cag aaa gta ggc att     448
Ala Trp Lys Leu Gly Ser Pro Gly Pro Arg Ser Gln Lys Val Gly Ile
 60                  65                  70 gct tgg gtg ctg cct cac ccc agg tat tct tgg aag gag gga acc cat     496
Ala Trp Val Leu Pro His Pro Arg Tyr Ser Trp Lys Glu Gly Thr His
 75                  80                  85                  90 gca gac att gcc ctg gtg cgc ctg gaa cac tcc atc cag ttc tct gag     544
Ala Asp Ile Ala Leu Val Arg Leu Glu His Ser Ile Gln Phe Ser Glu
                 95                 100                 105 cgg atc ctg ccc atc tgc cta cct gac tcc tct gtc cgt ctc cct ccc     592
Arg Ile Leu Pro Ile Cys Leu Pro Asp Ser Ser Val Arg Leu Pro Pro
            110                 115                 120 aag acc gac tgc tgg att gcc ggc tgg gga agc atc cag gat gga gtg     640
Lys Thr Asp Cys Trp Ile Ala Gly Trp Gly Ser Ile Gln Asp Gly Val
125                 130                 135 ccc ctg ccc cac cct cag acc ctt cag aag ctg aag gtg ccc atc atc     688
Pro Leu Pro His Pro Gln Thr Leu Gln Lys Leu Lys Val Pro Ile Ile
        140                 145                 150 gac tcc gaa ctc tgc aaa agc ttg tac tgg cgg gga gcc ggt cag gaa     736
Asp Ser Glu Leu Cys Lys Ser Leu Tyr Trp Arg Gly Ala Gly Gln Glu
155                 160                 165                 170 gcc atc acg gag ggc atg ctg tgt gct ggt tac ctg gaa ggg gag cgg     784
Ala Ile Thr Glu Gly Met Leu Cys Ala Gly Tyr Leu Glu Gly Glu Arg
                175                 180                 185 gat gct tgt ctg ggc gac tct ggg ggt ccc ctg atg tgc cag gtg gat     832
Asp Ala Cys Leu Gly Asp Ser Gly Gly Pro Leu Met Cys Gln Val Asp
            190                 195                 200 gac cac tgg cta ctg act ggc ata atc agc tgg gga gag ggc tgc gga     880
Asp His Trp Leu Leu Thr Gly Ile Ile Ser Trp Gly Glu Gly Cys Gly
        205                 210                 215 gcg caa ccg gcc cgg tgt gta cac cag cct cct agc tca ccg ctc ctg     928
Ala Gln Pro Ala Arg Cys Val His Gln Pro Pro Ser Ser Pro Leu Leu
220                 225                 230 ggt gca aag gat cgt tca agg ggt gca gct gcg cgg gta ctt ggc gga     976
Gly Ala Lys Asp Arg Ser Arg Gly Ala Ala Ala Arg Val Leu Gly Gly
235                 240                 245                 250 cag tgg gga cac agg aag ctc cta atc taggatctga agatgagcag          1023
Gln Trp Gly His Arg Lys Leu Leu Ile
                255 cctcctgcaa ttctctctgc tgtaaatatg tcttctacct ccgggggggcg cccgcggcct  1083 gagcgagaga acaaggaagt tctggaaccg cccacataga ggatccgccc ctcaatcgag   1143 gactctgtgt gtgtgtgtgt gtgtgtgtgt gtgtgtgcct ctgtgtgcgt gtgtatgcgc   1203 gcgcacgtgc gcgcgagagc aatgattttt tttttttacag ttatacgtaa ccatgcccac  1263 atatttattc cagtttcaat aaattatttta ttcttaaaaa aaaaaaaaaa aaaaaaaaa   1322

<210> SEQ ID NO 20
<211> LENGTH: 308
<212> TYPE: PRT
<213> ORGANISM: Mus. Sp.

<400> SEQUENCE: 20

Met Met Ile Ser Arg Pro Pro Ala Leu Gly Gly Asp Gln Phe Ser
                -45                 -40                 -35

Ile Leu Ile Leu Leu Val Leu Leu Thr Ser Thr Ala Pro Ile Ser Ala
```

-continued

```
            -30                 -25                 -20
Ala Thr Ile Arg Val Ser Pro Asp Cys Gly Lys Pro Gln Gln Leu Asn
            -15                 -10                 -5

Arg Ile Val Gly Gly Glu Asp Ser Met Asp Ala Gln Trp Pro Trp Ile
 -1   1               5                  10                  15

Val Ser Ile Leu Lys Asn Gly Ser His His Cys Ala Gly Ser Leu Leu
                 20                  25                  30

Thr Asn Arg Trp Val Val Thr Ala Ala His Cys Phe Lys Ser Asn Met
             35                  40                  45

Asp Lys Pro Ser Leu Phe Ser Val Leu Leu Gly Ala Trp Lys Leu Gly
         50                  55                  60

Ser Pro Gly Pro Arg Ser Gln Lys Val Gly Ile Ala Trp Val Leu Pro
     65                  70                  75

His Pro Arg Tyr Ser Trp Lys Glu Gly Thr His Ala Asp Ile Ala Leu
 80                  85                  90                  95

Val Arg Leu Glu His Ser Ile Gln Phe Ser Glu Arg Ile Leu Pro Ile
                100                 105                 110

Cys Leu Pro Asp Ser Ser Val Arg Leu Pro Pro Lys Thr Asp Cys Trp
            115                 120                 125

Ile Ala Gly Trp Gly Ser Ile Gln Asp Gly Val Pro Leu Pro His Pro
        130                 135                 140

Gln Thr Leu Gln Lys Leu Lys Val Pro Ile Ile Asp Ser Glu Leu Cys
    145                 150                 155

Lys Ser Leu Tyr Trp Arg Gly Ala Gly Gln Glu Ala Ile Thr Glu Gly
160                 165                 170                 175

Met Leu Cys Ala Gly Tyr Leu Glu Gly Glu Arg Asp Ala Cys Leu Gly
                180                 185                 190

Asp Ser Gly Gly Pro Leu Met Cys Gln Val Asp His Trp Leu Leu
            195                 200                 205

Thr Gly Ile Ile Ser Trp Gly Glu Gly Cys Gly Ala Gln Pro Ala Arg
        210                 215                 220

Cys Val His Gln Pro Pro Ser Ser Pro Leu Leu Gly Ala Lys Asp Arg
    225                 230                 235

Ser Arg Gly Ala Ala Ala Arg Val Leu Gly Gly Gln Trp Gly His Arg
240                 245                 250                 255

Lys Leu Leu Ile
```

<210> SEQ ID NO 21
<211> LENGTH: 99
<212> TYPE: DNA
<213> ORGANISM: Artificial Sequence
<220> FEATURE:
<223> OTHER INFORMATION: Designed oligonucleotide to construct plasmid
      pSecTrypHis

<400> SEQUENCE: 21
aagcttggct agcaacacca tgaatctact cctgatcctt acctttgttg ctgctgctgt      60
tgctgccccc tttgacgacg atgacaagga tccgaattc                            99

<210> SEQ ID NO 22
<211> LENGTH: 99
<212> TYPE: DNA
<213> ORGANISM: Artificial Sequence
<220> FEATURE:
<223> OTHER INFORMATION: Designed oligonucleotide to construct plasmid
      pSecTrypHis

| | |
|---|---|
| <400> SEQUENCE: 22 | |
| gaattcggat ccttgtcatc gtcgtcaaag ggggcagcaa cagcagcagc aacaaaggta | 60 |
| aggatcagga gtagattcat ggtgttgcta gccaagctt | 99 |

<210> SEQ ID NO 23
<211> LENGTH: 15
<212> TYPE: DNA
<213> ORGANISM: Artificial Sequence
<220> FEATURE:
<223> OTHER INFORMATION: Designed oligonucleotide primer to amplify
      neurosin-encoding sequence

| | |
|---|---|
| <400> SEQUENCE: 23 | |
| ttggtgcatg gcgga | 15 |

<210> SEQ ID NO 24
<211> LENGTH: 27
<212> TYPE: DNA
<213> ORGANISM: Artificial Sequence
<220> FEATURE:
<223> OTHER INFORMATION: Designed oligonucleotide primer to amplify
      neurosin-encoding sequence

| | |
|---|---|
| <400> SEQUENCE: 24 | |
| tcctcgagac ttggcctgaa tggtttt | 27 |

<210> SEQ ID NO 25
<211> LENGTH: 35
<212> TYPE: DNA
<213> ORGANISM: Artificial Sequence
<220> FEATURE:
<223> OTHER INFORMATION: Designed oligonucleotide primer to amplify
      a portion of plasmid pSecTrypHis/Neurosin

| | |
|---|---|
| <400> SEQUENCE: 25 | |
| gcgctagcag atctccatga atctactcct gatcc | 35 |

<210> SEQ ID NO 26
<211> LENGTH: 29
<212> TYPE: DNA
<213> ORGANISM: Artificial Sequence
<220> FEATURE:
<223> OTHER INFORMATION: Designed oligonucleotide primer to amplify
      a portion of plasmid pSecTrypHis/Neurosin

| | |
|---|---|
| <400> SEQUENCE: 26 | |
| tgaagcttgc catggaccaa cttgtcatc | 29 |

<210> SEQ ID NO 27
<211> LENGTH: 26
<212> TYPE: DNA
<213> ORGANISM: Artificial Sequence
<220> FEATURE:
<223> OTHER INFORMATION: Designed oligonucleotide primer to amplify
      a portion of plasmid pTrypHis

| | |
|---|---|
| <400> SEQUENCE: 27 | |
| ccaagcttca ccatcaccat caccat | 26 |

<210> SEQ ID NO 28
<211> LENGTH: 17
<212> TYPE: DNA
<213> ORGANISM: Artificial Sequence
<220> FEATURE:
<223> OTHER INFORMATION: Designed oligonucleotide primer to amplify
      a portion of plasmid pTrypSigTag

```
<400> SEQUENCE: 28
gcacagtcga ggctgat                                                    17

<210> SEQ ID NO 29
<211> LENGTH: 17
<212> TYPE: DNA
<213> ORGANISM: Artificial Sequence
<220> FEATURE:
<223> OTHER INFORMATION: Designed oligonucleotide primer to amplify
      a portion of plasmid pFBTrypSigTag

<400> SEQUENCE: 29
caaatgtggt atggctg                                                    17

<210> SEQ ID NO 30
<211> LENGTH: 20
<212> TYPE: DNA
<213> ORGANISM: Artificial Sequence
<220> FEATURE:
<223> OTHER INFORMATION: Designed oligonucleotide primer to amplify
      conserved region of serin proteases-encoding sequence
<220> FEATURE:
<221> NAME/KEY: misc_feature
<222> LOCATION: (9)..(9)
<223> OTHER INFORMATION: n is a, c, g or t.
<220> FEATURE:
<221> NAME/KEY: misc_feature
<222> LOCATION: (12)..(12)
<223> OTHER INFORMATION: n is a, c, g or t.

<400> SEQUENCE: 30
gtgctcacng cngcbcaytg                                                 20

<210> SEQ ID NO 31
<211> LENGTH: 20
<212> TYPE: DNA
<213> ORGANISM: Artificial Sequence
<220> FEATURE:
<223> OTHER INFORMATION: Designed oligonucleotide primer to amplify
      conserved region of serin proteases-encoding sequence
<220> FEATURE:
<221> NAME/KEY: misc_feature
<222> LOCATION: (12)..(12)
<223> OTHER INFORMATION: n is a, c, g or t.
<220> FEATURE:
<221> NAME/KEY: misc_feature
<222> LOCATION: (15)..(15)
<223> OTHER INFORMATION: n is a, c, g or t.

<400> SEQUENCE: 31
ccvctrwsdc cnccnggcga                                                 20

<210> SEQ ID NO 32
<211> LENGTH: 20
<212> TYPE: DNA
<213> ORGANISM: Artificial Sequence
<220> FEATURE:
<223> OTHER INFORMATION: Designed oligonucleotide primer designated
      as hBSSP4F1 for RACE for human BSSP4 (forward)

<400> SEQUENCE: 32
aggttcctat catcgactcg                                                 20

<210> SEQ ID NO 33
<211> LENGTH: 21
<212> TYPE: DNA
<213> ORGANISM: Artificial Sequence
<220> FEATURE:
```

```
<223> OTHER INFORMATION: Designed oligonucleotide primer designated as
      hBSSP4F2 for RACE for human BSSP4 (forward)

<400> SEQUENCE: 33
tgaggacatg ctgtgtgccg g                                         21

<210> SEQ ID NO 34
<211> LENGTH: 20
<212> TYPE: DNA
<213> ORGANISM: Artificial Sequence
<220> FEATURE:
<223> OTHER INFORMATION: Designed oligionucleotide primer designated as
      hBSSP4F3 to amplify mature human BSSP4-encoding region (forward)

<400> SEQUENCE: 34
gttgtgggcg gcgaggacag                                           20

<210> SEQ ID NO 35
<211> LENGTH: 20
<212> TYPE: DNA
<213> ORGANISM: Artificial Sequence
<220> FEATURE:
<223> OTHER INFORMATION: Designed oligonucleotide primer designated as
      hBSSP4F6 to amplify full-length human BSSP4-encoding mRNA
      (forward)

<400> SEQUENCE: 35
gccatggtgg tttctggagc                                           20

<210> SEQ ID NO 36
<211> LENGTH: 21
<212> TYPE: DNA
<213> ORGANISM: Artificial Sequence
<220> FEATURE:
<223> OTHER INFORMATION: Designed oligonucleotide primer designated as
      hBSSP4R1 for RACE for human BSSP4 (reverse)

<400> SEQUENCE: 36 tatggttttgt tcaggttgtc c                                        21

<210> SEQ ID NO 37
<211> LENGTH: 20
<212> TYPE: DNA
<213> ORGANISM: Artificial Sequence
<220> FEATURE:
<223> OTHER INFORMATION: Desinged oligonucleotide primer designated as
      hBSSP4R2 for RACE for human BSSP4 (reverse)

<400> SEQUENCE: 37
agggcaatgt ctgcacaggc                                           20

<210> SEQ ID NO 38
<211> LENGTH: 27
<212> TYPE: DNA
<213> ORGANISM: Artificial Sequence
<220> FEATURE:
<223> OTHER INFORMATION: Designed oligonucleotide primer designated as
      hBSSP4R3/E to amplify full-length human BSSP4-encoding mRNA
      (reverse)

<400> SEQUENCE: 38
ctgaattcct aggagcgcgc ggcggcc                                   27

<210> SEQ ID NO 39
<211> LENGTH: 28
<212> TYPE: DNA
<213> ORGANISM: Artificial Sequence
```

```
<220> FEATURE:
<223> OTHER INFORMATION: Designed oligonucleotide primer designated as
      hBSSP4R4/E to amplify full-length human BSSP4-encoding mRNA
      (reverse)

<400> SEQUENCE: 39
gagaattcga tatgtgggca gggttaca                                       28

<210> SEQ ID NO 40
<211> LENGTH: 21
<212> TYPE: DNA
<213> ORGANISM: Artificial Sequence
<220> FEATURE:
<223> OTHER INFORMATION: Designed oliginucleotide primer designated as
      mBSSP4.1 for RACE for mouse BSSP4 (forward)

<400> SEQUENCE: 40
acaaaccatc tctgttctca g                                              21

<210> SEQ ID NO 41
<211> LENGTH: 20
<212> TYPE: DNA
<213> ORGANISM: Artificial Sequence
<220> FEATURE:
<223> OTHER INFORMATION: Designed oligonucleotide primer designated as
      mBSSP4F2 for RACE for mouse BSSP4 (forward)

<400> SEQUENCE: 41
gtcccagaaa gtaggcattg                                                20

<210> SEQ ID NO 42
<211> LENGTH: 20
<212> TYPE: DNA
<213> ORGANISM: Artificial Sequence
<220> FEATURE:
<223> OTHER INFORMATION: Designed oligonucleotide primer designated as
      mBSSP4F3 to amplify full-length mouse BSSP4-encoding mRNA
      (forward)

<400> SEQUENCE: 42
ctccacccat accagcaatg                                                20

<210> SEQ ID NO 43
<211> LENGTH: 20
<212> TYPE: DNA
<213> ORGANISM: Artificial Sequence
<220> FEATURE:
<223> OTHER INFORMATION: Designed oligonucleotide primer designated as
      mBSSP4F4 to amplify mature mouse BSSP4-encoding region (forward)

<400> SEQUENCE: 43
attgtgggag gtgaggacag                                                20

<210> SEQ ID NO 44
<211> LENGTH: 20
<212> TYPE: DNA
<213> ORGANISM: Artificial Sequence
<220> FEATURE:
<223> OTHER INFORMATION: Designed oligonucleotide primer designated as
      mBSSP4.2 for RACE for mouse BSSP4 (reverse)

<400> SEQUENCE: 44
tgcagagttc ggagtcgatg                                                20

<210> SEQ ID NO 45
<211> LENGTH: 20
<212> TYPE: DNA
```

```
<213> ORGANISM: Artificial Sequence
<220> FEATURE:
<223> OTHER INFORMATION: Designed oligonucleotide primer designated as
      mBSSP4R2 for RACE for mouse BSSP4 (reverse)

<400> SEQUENCE: 45
atccagcagt cggtcttggg                                                 20

<210> SEQ ID NO 46
<211> LENGTH: 30
<212> TYPE: DNA
<213> ORGANISM: Artificial Sequence
<220> FEATURE:
<223> OTHER INFORMATION: Designed oligonucleotide primer designated as
      mBSSP4R3/P to amplify full-length mouse BSSP4-encoding mRNA
      (reverse)

<400> SEQUENCE: 46
attctgcagt tccttgttct ctcgctcagg                                      30

<210> SEQ ID NO 47
<211> LENGTH: 117
<212> TYPE: DNA
<213> ORGANISM: Artificial Sequence
<220> FEATURE:
<223> OTHER INFORMATION: Designed oligonucleotide to construct plasmid
      pTrypHis

<400> SEQUENCE: 47
aagcttggct agcaacacca tgaatctact cctgatcctt acctttgttg ctgctgctgt     60
tgctgccccc tttcaccatc accatcacca tgacgacgat gacaaggatc cgaattc      117

<210> SEQ ID NO 48
<211> LENGTH: 117
<212> TYPE: DNA
<213> ORGANISM: Artificial Sequence
<220> FEATURE:
<223> OTHER INFORMATION: Designed oligonucleotide to construct plasmid
      pTrypHis

<400> SEQUENCE: 48
gaattcggat ccttgtcatc gtcgtcatgg tgatggtgat ggtgaaaggg ggcagcaaca     60
gcagcagcaa caaaggtaag gatcaggagt agattcatgg tgttgctagc caagctt      117

<210> SEQ ID NO 49
<211> LENGTH: 73
<212> TYPE: DNA
<213> ORGANISM: Artificial Sequence
<220> FEATURE:
<223> OTHER INFORMATION: Synthetic

<400> SEQUENCE: 49
cccgggcccc agcgcttttg tgtatataaa tgttaatgat ttttataggt atttgtaacc     60
ctgcccacat atc                                                       73

<210> SEQ ID NO 50
<211> LENGTH: 11
<212> TYPE: PRT
<213> ORGANISM: Artificial Sequence
<220> FEATURE:
<223> OTHER INFORMATION: Synthetic

<400> SEQUENCE: 50

Pro Gly Pro Gln Arg Phe Cys Val Tyr Lys Cys
1               5                   10
```

```
<210> SEQ ID NO 51
<211> LENGTH: 5
<212> TYPE: PRT
<213> ORGANISM: Artificial Sequence
<220> FEATURE:
<223> OTHER INFORMATION: Synthetic

<400> SEQUENCE: 51

Asp Asp Asp Asp Lys
1               5

<210> SEQ ID NO 52
<211> LENGTH: 4
<212> TYPE: PRT
<213> ORGANISM: Artificial Sequence
<220> FEATURE:
<223> OTHER INFORMATION: Synthetic

<400> SEQUENCE: 52

Leu Val His Gly
1
```